(12) United States Patent
Agadjanyan et al.

(10) Patent No.: US 7,579,452 B2
(45) Date of Patent: Aug. 25, 2009

(54) CANCER VACCINE BASED ON BROTHER OF REGULATOR OF IMPRINTED SITES MOLECULE

(75) Inventors: Michael G Agadjanyan, Huntington Beach, CA (US); Anahit Ghochikyan, Huntington Beach, CA (US)

(73) Assignee: OncoMune, LLC, Hollywood, FL (US)

( * ) Notice: Subject to any disclaimer, the term of this patent is extended or adjusted under 35 U.S.C. 154(b) by 0 days.

(21) Appl. No.: 10/569,907

(22) PCT Filed: Aug. 25, 2004

(86) PCT No.: PCT/US2004/027856
§ 371 (c)(1),
(2), (4) Date: Feb. 27, 2006

(87) PCT Pub. No.: WO2005/021029
PCT Pub. Date: Mar. 10, 2005

(65) Prior Publication Data
US 2006/0286115 A1    Dec. 21, 2006

Related U.S. Application Data

(60) Provisional application No. 60/497,511, filed on Aug. 25, 2003.

(51) Int. Cl.
*C07H 21/04* (2006.01)
*C12N 15/00* (2006.01)
*A61K 48/00* (2006.01)

(52) U.S. Cl. ............... 536/23.5; 514/44; 435/320.1

(58) Field of Classification Search .............. None
See application file for complete search history.

(56) References Cited

U.S. PATENT DOCUMENTS

2005/0182249 A1 *  8/2005  Lobanenkov et al. ...... 536/23.5

OTHER PUBLICATIONS

Stedman's Medical Dictionary, p. 1, "vaccine".*
Stedman's Medical Dictionary, p. 1, "immunize".*
MSN Encarta Dictionary, p. 1, "immunize".*
Ghochikyan et al ( J of Immunology, 2007, 178:566-573).*
Loukinov at al I (J of Cellular Biochemistry, 2006, 98:1037-1043).*
Vatolin et al (Cancer Research, 2005, 65:7751-7762).*
Loukinov et al II (PNAS, 2002, 99:6806-6811).*
Filippova et al (Cancer Research, 2002. 62:48-52).*
Loukinov at al (J of Cellular Biochemistry, 2006, 98:1037-1043).*
Mkrtichyan et al (Gene Therapy, 2008, 15:61-64).*
Sela, M., et al., Therapeutic vaccines: realities of today and hopes for tomorrow, PNAS, (2004), vol. 10, p. 14559.
Arora, D.R., et al., HIV-1 therapeutic vaccine: a ray of hope, Indian J Med Microbiol., (2003), vol. 21, pp. 225-232.
Robbins, G.K., Augmentation of HIV-1 specific T helper cell responses in chronic HIV-1 infection by therapeutic immunization, AIDS, (2003), vol. 17, pp. 1121-1126.

* cited by examiner

*Primary Examiner*—Laura B Goddard
(74) *Attorney, Agent, or Firm*—The Law Office of Jane K. Babin, Professional Corporation; Jane K. Babin

(57) ABSTRACT

Polynucleotides encoding a nonfunctional mutant form of the Brother of Regulator of Imprinted Sites (BORIS) molecule, nonfunctional mutated BORIS protein, polypeptide or peptide and modified protein forms of BORIS are described. These molecules are used as a therapeutic vaccine against cancer.

24 Claims, 6 Drawing Sheets

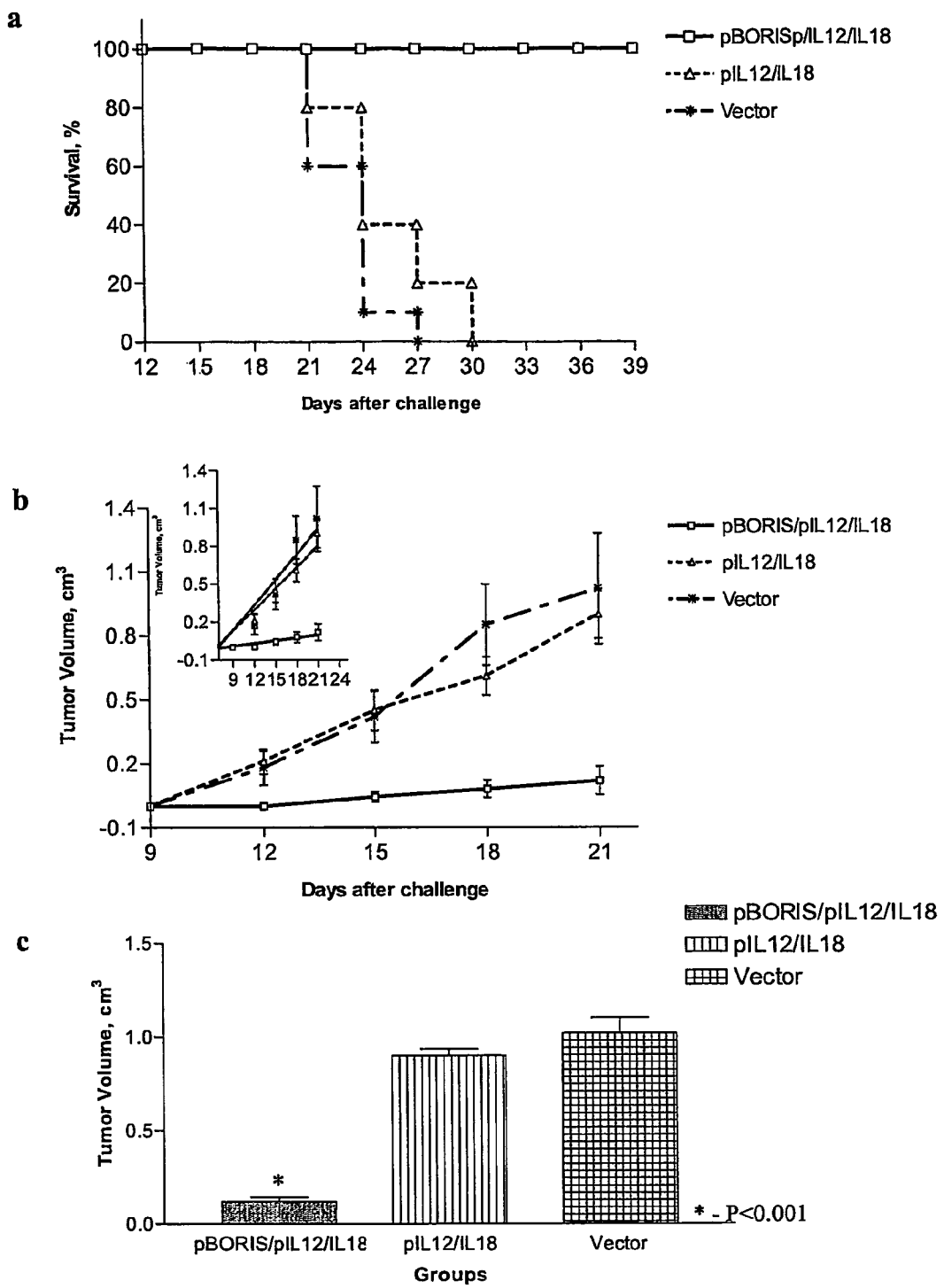

Figure 1. Vaccination of mice (n=10) with pBORIS plus pIFNγ or pIL12/IL18 resulted in protection of mice from challenge with $10^4$ 4T1 tumor cells. Although, 50% of mice from group immunized with pBORIS mixed with pIL12/IL18 generated small tumors (~0.2cm$^3$)(b) they all survived by day 39, when all experimental mice died almost 10 days ago (a). Significant difference in tumor volume at day 21 were determined between groups pBORIS/pIL12/pIL18 vs. pIL12/pIL18 and vector, * P<0.001)(c).

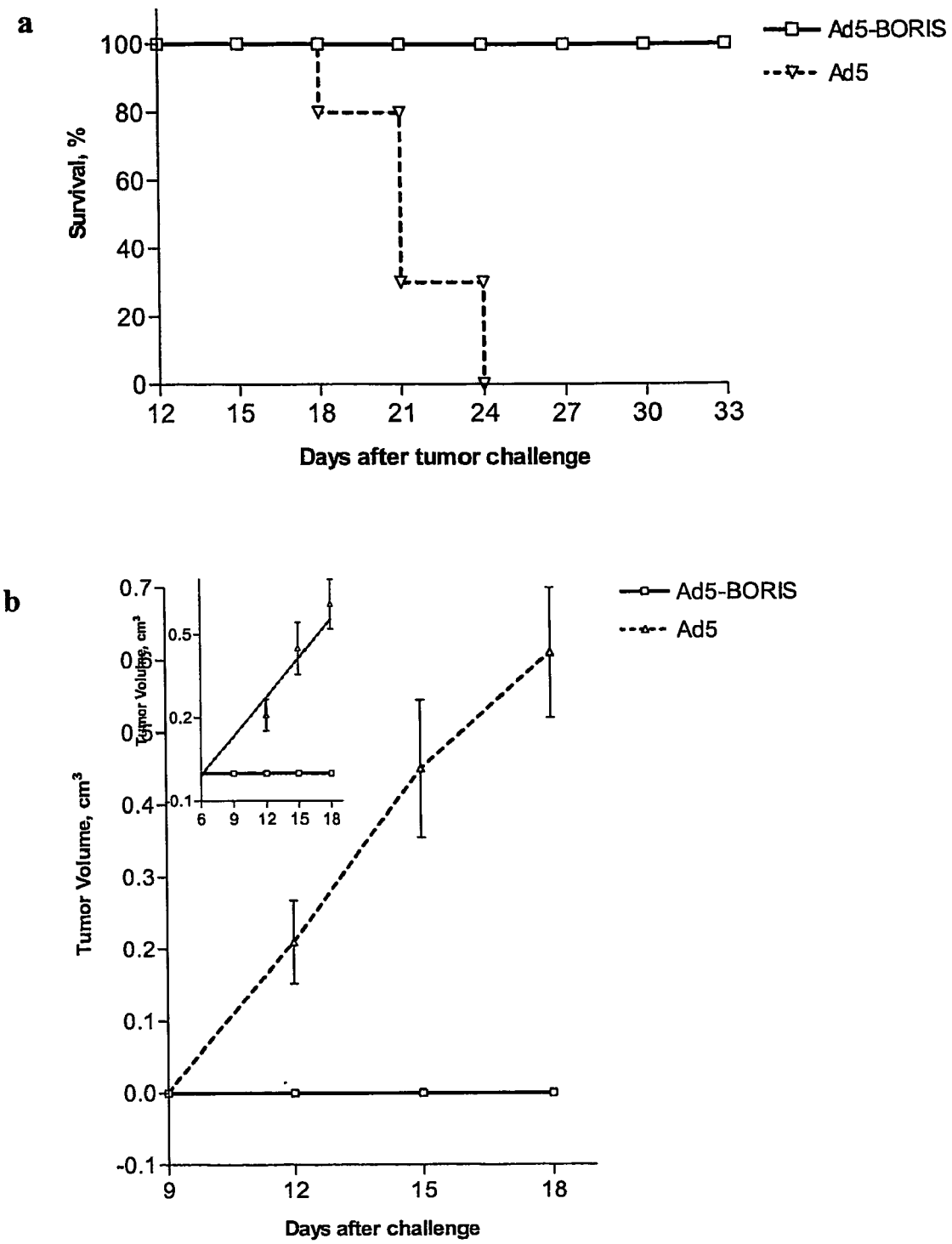
Figure 2. Vaccination of mice (n=10) with pBORIS followed by Ad5-BORIS resulted in protection of mice from challenge with $10^4$ 4T1 cells.

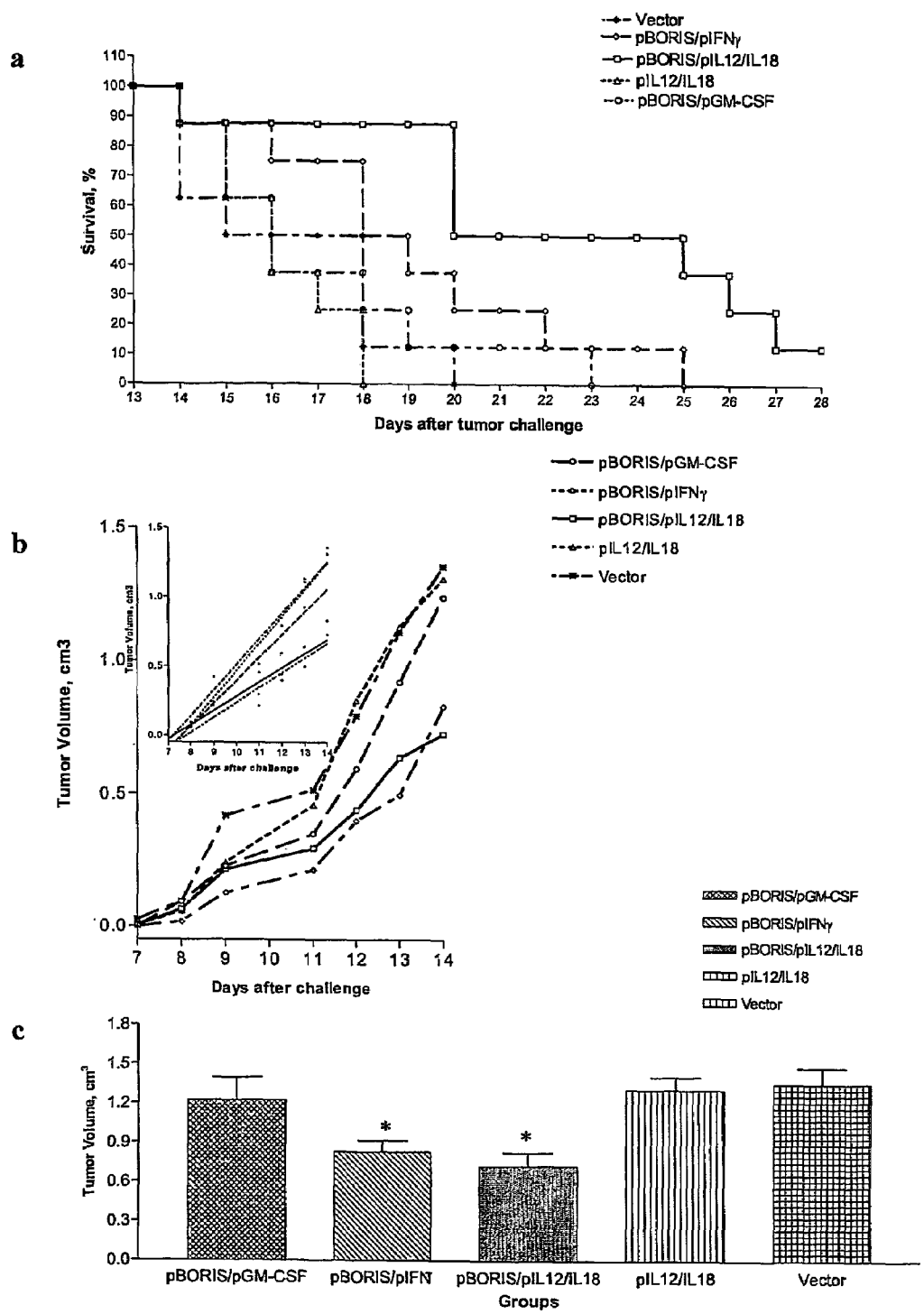

Figure 3. Gene-gun immunization of mice (n=8) with pBORIS plus pIFNγ or pIL12/IL18 followed by challenge with $10^5$ 4T1 tumor cells significantly prolonged the survival of mice, significant difference were determined between groups pBORIS/pIL12/pIL18 vs. pIL12/pIL18 and vector, * P<0.001) (a), lower the tumor growth rate (b) and prolonged the time of tumor growth to the volume of $2cm^3$. Significant difference in tumor volume at day 14 was determined between groups pBORIS/pIFNγ vs. vector (p<0.05), pBORIS/pIL12/IL18 vs. pIL12/IL18 (P<0.05), pBORIS/pIL12/IL18 vs. vector (P<0.01) (c). On day 20, when mice in the control groups died from tumor growth, 50% of mice immunized with pBORIS/pIL12/pIL18 and 25% of mice immunized with pBORIS/pIFNγ were still alive.

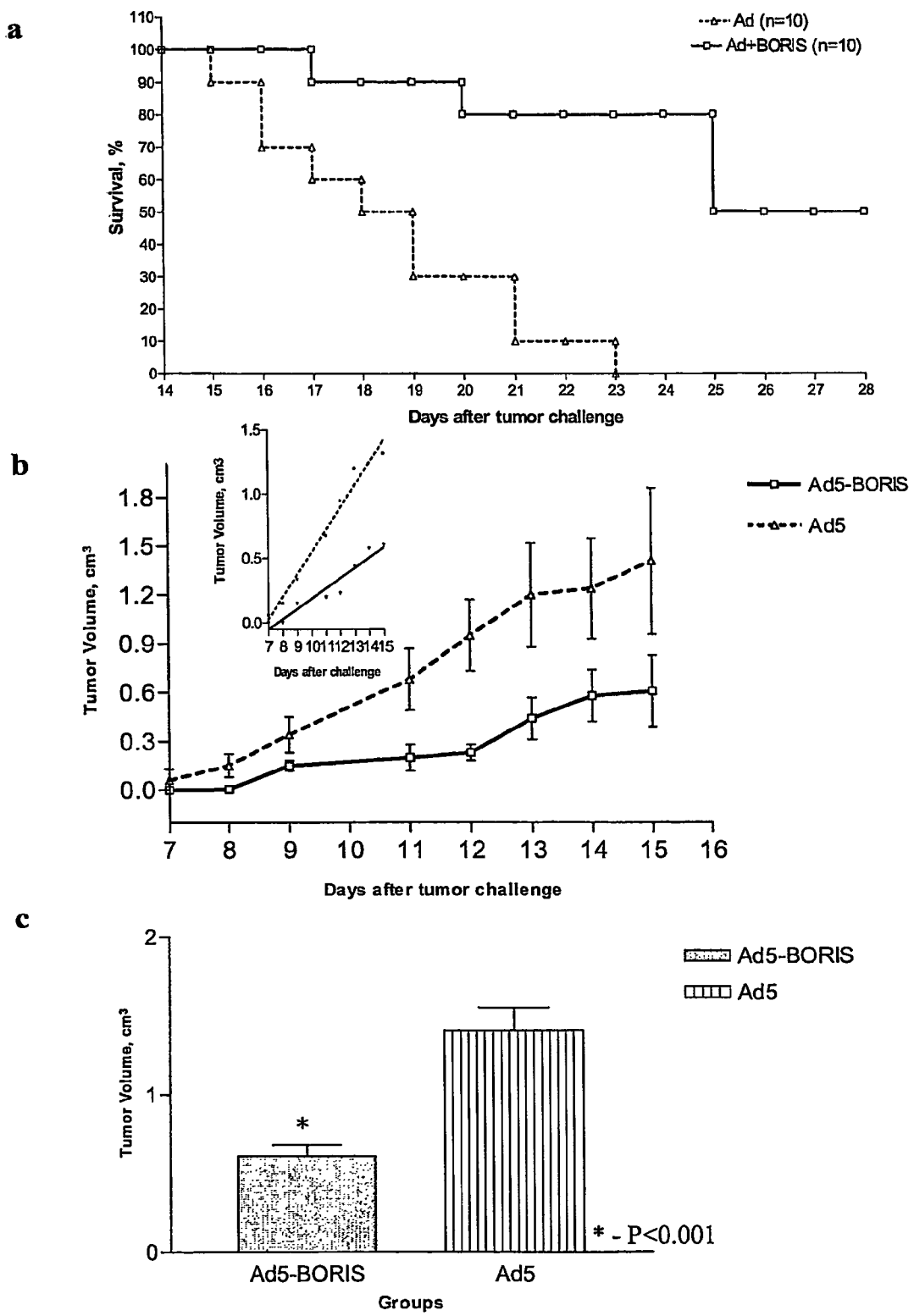

Figure 4. Vaccination of mice (n=10) with pBORIS followed by injection of Ad5-BORIS significantly prolonged the survival of mice (a), lower the tumor growth rate (b) and prolonged the time of tumor growth to the volume of 2cm$^3$ after challenge of mice with $10^5$ 4T1 tumor cells. Significant difference in tumor volume at day 15 was determined between groups Ad5-BORIS vs. Ad5 P<0.001(c). On day 23, when mice in the control groups died from tumor growth, 80% of mice immunized with Ad5-BORIS were alive and had significantly smaller size of tumors.

```
MAAAEVPVPSGYFTQIKEQKLKPGDLEEEKEEDGVQRVEAQEGVVKEVEAENSCLLLEAR       60
MAATEISVLSEQFTKIKELELMPEKGLKEEEKDGVCR-EKDHRSPSELEAERTSGAFQDS       59

..........APV-ESDRRILTLQTVHLESQDVHLQGLGWLSVPHSEELSGTVPEAEGIL      109
VLEEEVELVLAPSEESEKYILTLQTVHFTSEAVELQDMSLLSIQQEGVQ-VVVQQPG--       116

QLPSVLWLDPEPQLSLQHCVTVSIPEELYPPEELQRIHFHLLRENVLMAEENPELTPDLD     169
--PGLLWLEEGPRQSLQQCVAISIQQELYSPQEMEVLQFHALEENVMVASEDSKLAVSLA     174

ESTAL-KKPEEDEKDQLPPQGETDKREERLLLLEMKPKEGKDDEIVLTISHLSLEEQQDP     228
ETAGLIKLEEEQEKNQL----LAERTKEQLFFVETMSGDERSDEIVLTVSNSNVEEQEDQ     230

ZF1
PAANQTSVPGAKAAKPKRRRQTKGKPQSFQCDTCPFTSSKLSTFNRHIKIHSNERPHL       286
PTAGQADAEKAKSTKNQRK--TKGAKGTFHCDVCMFTSSRMSSFNRHMKTHTSEKPHL       286
        ZF2                            ZF3
CHLCLKAFRTVTLLRNHVNTHTGTRPHKCRDCDMAFVTSGELVRHRRYKHTYEKPFK        343
CHLCLKTFRTVTLLRNHVNTHTGTRPYKCNDCNMAFVTSGELVRHRRYKHTHEKPFK        343
        ZF4                            ZF5
CSLCKYASVEASKMKRHIRSHTGERPFQCCQCAYASRDSYKLKRHMRTHSGEKPYE         399
CSMCKYASVEASKLKRHVRSHTGERPFQCCQCSYASRDTYKLKRHMRTHSGEKPYE         399
        ZF6                            ZF7
CPTCHVRFTQSGTMKIHIAQKHGENVPKYECPHCATIIARKSDLRVHLRNLHSQSPEEMK     459
CHICHTRFTQSGTMKIHILQKHGENVPKYQCPHCATIIARKSDLRVHMRNLHAYSAAELK     459
        ZF8                            ZF9
CRYCPAGFHERYALIQHQRTHKNEKKFKCKQCDYACKQERCLKAHMRNHTGEKPFS         515
CRYCSAVFHERYALIQHQKTHKNEKRFKCKHCSYACKQERHMTAHIRTHTGEKPFT         515
        ZF10                           ZF11
CLACNKHFRQKQLLTVHLRKYHDPNFVPNLHLCLKCDKRFSRWSNLQRHRKKCDP-         570
CLSCNKCFRQKQLLNAHFRKYHDANFIPTVYKCSKCGKGFSRWINLHRHSEKCGSG         571

FHFTLAPNKDRRPVTRTQASEGEAGHKEGEPQCP................              604
EAKSAASGKGRRTRKRKQTILKEATKGQKEAAKGWKEAANGDEAAAEEASTTK            624

GEQALGHQGEAAGSQSP.......DHGLTCEMIFNMMDK                          636
GEQFPGEMFPVACRETTARVKEEVDEGVTCEMLLNTMDK                          663
```

Figure 5

CANCER VACCINE BASED ON BROTHER OF REGULATOR OF IMPRINTED SITES MOLECULE

This application is a National Phase under 35 U.S.C § 371 of PCT International Application No. PCT/US2004/027856 which has an International filing date of Aug. 25, 2004, which designated the United States of America. In addition, this National Phase PCT application claims priority under 35 U.S.C. 119(e) on U.S. Provisional Application No(s). 60/497,511 filed on Aug. 25, 2003.

FIELD OF THE INVENTION

The present invention relates to compositions and methods used for the generation of a tumor vaccine.

BACKGROUND

Vertebrates possess the ability to mount an immune response as a defense against pathogens from the environment as well as against aberrant cells, such as tumor cells, which develop internally. The immune response is the result of complex interactions between a variety of cells and factors, but generally comprises two main facets. One is a cellular component, in which specialized cells directly attack an offending agent (bearing an antigen) while the other is a humoral component, in which antibody molecules bind specifically to the antigen and aid in its elimination. Acting in concert, the individual elements are quite effective in limiting the initial onslaught of invading pathogens and eliminating them from the host.

The primary cells involved in providing an immune response are lymphocytes, which generally comprise two principal classes. The first of these, designated B cells or B lymphocytes, are typically generated in bone marrow and are, among other duties, responsible for producing and secreting antibodies. B cell antibody products tend to react directly with foreign antigens and neutralize them or activate other components of the immune systems that then eliminate them. In particular, opsonizing antibodies bind to extracellular foreign agents thereby rendering them susceptible to phagocytosis and subsequent intracellular killing. On the other hand, T cells or T lymphocytes, which generally develop or mature in the thymus, are responsible for mediating the cellular immune response. These cells do not recognize whole antigens but, instead, respond to short peptide fragments thereof bound to specialized proteins that appear on the surface of the surface of a target cell as well as an antigen presenting cell. More particularly, it appears that proteins produced within the cell, or taken up by the cell from extracellular milieu, are continually degraded to peptides by normal metabolic pathways. The resulting short fragments associate with intracellular major histocompatibility complex (MHC) molecules and the MHC-peptide complexes are transported to the surface of the cell for recognition by T cells. Thus, the cellular immune system is constantly monitoring a full spectrum of proteins produced or ingested by the cells and is posed to eliminate any cells presenting foreign antigens or tumor antigens; i.e. virus infected cells or cancer cells.

The structure of immunoglobulin G (IgG) is that of a tetrameric protein complex comprising two identical heavy (H) chains and two identical immunoglobulin light (L) chains. These chains are joined together by disulfide bonds to form the Y-shaped antibody complex. In solution however, the molecule takes on a more globular shape and readily bind to foreign antigens present in biological fluids. Amino acid sequence analysis of immunoglobulins has led to the definition of specific regions with various functional activities within the chains. Each light chain and each heavy chain has a variable region ($V_L$ and $V_H$ respectively) defined within the first 110 amino terminal residues. Three dimensional pairing of the $V_L$ and $V_H$ regions constitute the antigen-recognition portion or "antigen combining site" ("ACS") of immunoglobulin molecule. Because of the tetrameric nature of immunoglobulins, there are two identical antigen combining sites per molecule. The variable domains of these chains are highly heterogeneous in sequence and provide the diversity for antigen combining sites to be highly specific for a large variety of antigenic structures. The heterogeneity of the variable domains is not evenly distributed throughout the variable regions, but is located in three segments, called complementarity determining regions ("CDRs") designated CDR 1, CDR 2 and CDR 3. For further information regarding these structures see Watson et al., 1987, Molecular Biology of the Gene, Fourth Edition, Benjamin/Cummings Publishing Co., Inc. Menlo Park, Calif. incorporated herein by reference.

Each of the heavy chains also includes a constant region defining a particular isotype and assigns the immunoglobulin to one of the immunoglobulin classes and subclasses. The constant region contains units called domains (i.e. $C_{H1}$, $C_{H2}$, etc.) that do not vary significantly among antibodies of a single class. The constant region does not participate in antigen binding, but can be associated with a number of biological activities known as "effector functions", such as binding to Fc receptors on cell surfaces as well as binding to complement proteins. Antigen presenting cells such as dendritic cells and macrophages are, among other features, generally distinguished by the presence of an Fc receptor. Consequently, if an antibody is bound to a pathogen, it can then link to a phagocyte via the Fc portion. This allows the pathogen to be ingested and destroyed by the phagocyte, a process known as opsonization. Moreover, as will be discussed in more detail below, various pathogenic antigens may be processed and displayed by the APC to further stimulate an immune response.

Unlike the heavy chains, the light chains have a single constant domain ($C_L$). A light chain pairs with a heavy chain through a disulfide bond which attaches heavy constant region $C_{H1}$ to $C_L$. In addition, the heavy chains have a hinge region separating constant regions $C_{H1}$ and $C_{H2}$ from the remainder of the molecule. It is this hinge region that is largely responsible for the flexibility of the tetramer. The two heavy chains of the molecule pair together through disulfide bonds at the junction between the hinge region and $C_{H2}$.

In order to provide such an extensive repertoire, immunoglobulin genes have evolved so as permit the production of vast numbers of different immunoglobulin proteins from a finite number of genes i.e. inherent polymorphism. Due to inherent polymorphism, mammals are able to produce antibodies to a seemingly infinite variety of antigens. For a review of immunoglobulin genetics and protein structure see Lewin, "Genes III", John Wiley and Sons, N.Y. (1987) and Benjamini and Leskowitz, 1988, Immunology, Alan R. Liss, Inc., New York, which is incorporated herein by reference.

In the past few years antibodies have become extremely important in diagnostic and therapeutic applications due to their diversity and specificity. Increasingly, molecular biology techniques have been used to expand the variety and availability of antibodies for scientific applications. For instance, a single antibody producing B cell can be immortalized by fusion with a tumor cell and expanded to provide an in vitro source of antibodies of a single specificity known as a "monoclonal antibody" (mAb). Such an immortal B cell line is termed a "hybridoma."

Until recently, the source of most mAb has been murine (mouse) hybridomas cultured in vitro. That is, a mouse was typically injected with a selected antigen or immunogen. Subsequently, the animal was sacrificed and cells removed from its spleen were fused with immortal myeloma cells. Although they have been used extensively in diagnostic procedures, murine mAb are not well suited for therapeutic applications in most mammals including humans. In part, this is due to the fact that murine antibodies are recognized as foreign by other mammalian species and elicit an immune response that may itself cause illness.

To overcome at least some of the problems of immune responses generated by foreign mAb and the lack of suitable human mAb, genetic engineering has been used to construct humanized chimeric immunoglobulin molecules which contain the antigen binding complementarity determining regions of the murine antibodies but in which the remainder of the molecule is composed of human antibody sequences which are not recognized as foreign. Such antibodies have been used to treat tumors as the mouse variable region recognizes the tumor antigen and the humanized portion of the molecule is able to mediate an immune response without being rapidly eliminated by the body. See, for example, Jones et al., Nature, 321:522-525 (1986), which is incorporated herein by reference.

Other uses of such antibodies are detailed in PCT Publication No. WO 94/14847, which is also incorporated herein by reference. In these cases epitopes of foreign antigens such as viral or bacterial epitopes are grafted onto the hypervariable region of an immunoglobulin to induce a response. That is, the engineered antibodies are used as a vaccine to provoke an immune response and confer long-term immunogenic memory thereby allowing the subject to fight off subsequent infections.

These and more traditional vaccines are effective in that they stimulate both prongs of the immune system. Despite the intricacies associated with the humoral component of the immune response, it would not, in and of itself, be capable of effectively protecting an animal from the myriad pathogenic assaults to which it is subject each day. Rather, it is only the presence of a highly evolved cellular response that allows higher organisms to survive and proliferate.

As indicated above, T lymphocytes or T cells, which arise from precursors in the bone marrow, are central players in the immune response against invading viruses and other microbes. The progenitor stem cells migrate to the thymus where, as so-called thymocytes, they become specialized. In particular, they begin to display the receptor molecules that later enable mature T cells to detect infection To be beneficial, T cells must be able to attach through their receptors to antigens (protein markers signaling an invader's presence). At the same time, they should be blind to substances made by the body as self-reactive T cells can destroy normal tissues. Typically, only those thymocytes that make useful receptors will mature fully and enter the bloodstream to patrol the body. Others that would be ineffectual or would attack the body's own tissue are, in healthy individuals, eliminated through apoptosis prior to leaving the thymus.

Mature T cells that finally enter the circulation, either as cytolytic T lymphocytes or T helper cells, remain at rest unless they encounter antigens that their receptors can recognize. Upon encountering the specific antigens for which the lymphocytes have affinity, they proliferate and perform effector functions, the result of which is elimination of the foreign antigens.

T cells have been classified into several subpopulations based on the different tasks they perform. These subpopulations include helper T cells ($T_h$), which are required for promoting or enhancing T and B cell responses; cytotoxic (or cytolytic) T lymphocytes (CTL), which directly kill their target cells by cell lysis; and suppressor or regulatory T cells ($T_s$ or Tr) which down-regulate the immune response. In every case T cells recognize antigens, but only when presented on the surface of a cell by a specialized protein complex attached to the surface of antigen presenting cells. More particularly, T cells use a specific receptor, termed the T cell antigen receptor (TCR), which is a transmembrane protein complex capable of recognizing an antigen in association with the group of proteins collectively termed the major histocompatibility complex (MHC). Thousands of identical TCR's are expressed on each cell. The TCR is related, both in function and structure, to the surface antibody (non-secreted) which B cells use as their antigen receptors. Further, different subpopulations of T cells also express a variety of cell surface proteins, some of which are termed "marker proteins" because they are characteristic of particular subpopulations. For example, most $T_h$ cells express the cell surface CD4 protein, whereas most CTL cells express the cell surface CD8 protein and Tr cells expressed CD25 and CD4 molecules. These surface proteins are important in the initiation and maintenance of immune responses that depend on the recognition of, and interactions between, particular proteins or protein complexes on the surface of APCs.

For some time it has been known that the major histocompatibility complex or MHC actually comprises a series of glycosylated proteins comprising distinct quaternary structures. Generally, the structures are of two types: class I MHC which displays peptides from proteins made inside the cell (such as self-proteins or proteins produced subsequent to viral replication), and class II MHC, which generally displays peptides from proteins that have entered the cell from the outside (soluble antigens such as bacterial toxins). Recognition of various antigens is assured by inherited polymorphism that continuously provides a diverse pool of MHC molecules capable of binding any pathogenic peptides that may arise. Essentially, all nucleated cells produce and express class I MHC, which may exhibit naturally occurring peptides, tumor associated peptides or peptides produced by a viral invader. Conversely, some other nucleated cells and among them specialized lymphoid cells, those generally known as antigen presenting cells, produce and express class II MHC proteins. Regardless of the cell type, both classes of MHC carry peptides to the cell surface and present them to resting T lymphocytes. Ordinarily, $T_h$ cells recognize class II MHC-antigen complexes while CTL's tend to recognize class I MHC-antigen complexes, although cross-presentation of antigens also occurred When a resting T cell bearing the appropriate TCR encounters the APC displaying the peptide on its surface, the TCR binds to the peptide-MHC complex. More particularly, hundreds of TCR's bind to numerous peptide-MHC complexes. When enough TCRs are contacted the cumulative effect activates the T cell. Receptors on T cells that are responsible for the specific recognition of, and response to, the MHC-antigen complex are composed of a complex of several integral plasma membrane proteins. As with the MHC complex previously discussed, a diverse pool of TCR's is assured by inherent polymorphism leading to somatic rearrangement. It should be emphasized that, while the pool of TCR's may be diverse, each individual T cell only expresses a single specific TCR. However, each T cell typically exhibits thousands of copies of this receptor, specific for only one peptide, on the surface of each cell. In addition, several other types of membrane associated proteins are involved with T cell binding and activation.

Activation of the T cell entails the generation of a series of chemical signals (primarily cytokines) that result in the cell taking direct action or stimulating other cells of the immune system to act. In the case of class I MHC-antigen activation, CTL's proliferate and act to destroy infected cells presenting the same antigen. Killing an infected cell deprives a virus of life support and makes it accessible to antibodies, which finally eliminate it. In contrast, activation of $T_h$ cells by class II MHC-antigen complexes does not destroy the antigen presenting cell (which is part of the host's defense system) but rather stimulates the $T_h$ cell to proliferate and generate signals (again primarily cytokines) that affect various cells. Among other consequences, the signaling leads to B cell stimulation, macrophage activation, CTL differentiation and promotion of inflammation. This concerted response is relatively specific and is directed to foreign elements bearing the peptide presented by the class II MHC system.

Constant surveillance of epitopes throughout those structures in the body accessible to the immune system provides a very effective means for recognizing and maintaining "self" and destroying epitopes and their carriers that invade the body or arise pathologically. When operating properly the immune response is surprisingly effective at eliminating microscopic pathogens and neoplastic (tumor) cells that are believed to arise continuously in the body and for the most part are eliminated by the immune system before becoming detectable. Certain regions of the body, such as the brain, eye, and testis, are protected from immune surveillance, these sites are referred to as immune privileged. In general, the complicated mechanisms for self-recognition are very efficient and allow a strong response to be directed exclusively at foreign antigens. Unfortunately, the immune system occasionally malfunctions and turns against the cells of the host provoking an autoimmune response. Typically, autoimmunity is held to occur when the antigen receptors on immune cells recognize specific antigens on healthy cells and cause the cells bearing those particular substances to die. In many cases, autoimmune reactions are self-limited in that they disappear when the antigens that set them off are cleared away. However, in some instances the autoreactive lymphocytes survive longer than they should and continue to induce apoptosis or otherwise eliminate normal cells.

Current data indicates that immune protection against all cancers requires the generation of a potent cellular immune responses against a unique tumor antigen expressed by the malignant cell. As a consequence, successful immune protection first requires a unique antigen expressed in the tumor cells (tumor-specific antigen) and second, induction of a potent T cell immune response targeted to the tumor antigen.

Several tumor-associated antigens are currently known, and have been used in pre-clinical and clinical studies for generating vaccines. For example, PSMA, PAP and PSA are antigens expressed in prostate tumor cells. Her2/neu and MUC1 are antigens expressed by breast cancer cells and other carcinomas, including carcinomas of the lung, ovary, colon, and pancreas. MAGEs and MART-1 are melanoma tumor cell-associated antigens, and CEA is an antigen associated with pancreas or colorectal cancer. Other tissue and/or tumor specific antigens also have been described. However, while all of these antigens are expressed in tumor cells in the normal or aberrant forms, they are also expressed in a variety of normal cells, and thus cannot be used for prophylactic vaccination. In other words, these tumor-associated antigens are still recognized by immune cells as self-molecules and so no true activation of the immune system occurs. This presents at least two obstacles for targeting these tumor-associated molecules as the basis for a vaccine. The first obstacle is the unresponsiveness (tolerance) of the immune system to self-molecules, which restricts its ability to generate potent cellular immune responses. The second is that any potent cellular immune response generated should not be directed toward normal cells that express the target antigen. This is the reason that all the tumor-associated antigens discussed above are suggested for use only as targets for therapeutic vaccinations.

A new protein has been recently described that is able to overcome the problems associated with the known tumor-associated antigens. Brother of Regulator of Imprinted Sites (BORIS) was first described as a DNA-binding protein found in testis. This protein shares 11 zinc-finger (ZF) domains with CCCTC-binding factor (CTCF) that is a multivalent 11-zinc finger nuclear factor. CTCF is a conserved, ubiquitous and highly versatile factor involved in various aspects of gene regulation and which forms methylation-sensitive insulators that regulate X chromosome inactivation and expression of imprinted genes. BORIS differs from CTCF, however, at the N and C termini and is expressed in a mutually exclusive manner with CTCF during male germ cell development. BORIS expression is restricted to the testis and then only within a select cell subpopulation of spermatocytes that are involved with the re-setting of methylation marks during male germ cell development. This testis cell subpopulation is also the only normal cell type known that does not express CTCF. Because inhibition of CTCF expression in cultured cells leads to apoptosis, it is reasonable to assume that BORIS is activated to maintain some of the vital CTCF functions in testis cells (Loukinov et al. (2002) Proc. Natl. Acad. Sci. 99(10): 6806-6811; which is incorporated herein by reference).

More recently, it was demonstrated that while CTCF overexpression also blocks cell proliferation, expression of BORIS in normally BORIS-negative cells promotes cell growth that can lead to transformation (Klenova et al. (2002) Cancer Biol. 12:399-414; which is incorporated herein by reference). Human BORIS maps to the 20q13 region, which is well known for frequent gains and/or amplifications observed in many of the same types of tumors that also often show loss of heterozygosity (LOH) at the paralogous locus on 16q22 where CTCF resides. These regions are associated with "hot-spots" associated with breast, prostate, ovarian, gastric, liver, endometrial, glioma, colon and esophageal cancer as well as Wilms tumors. Importantly, abnormal activation of BORIS expression appears to be found in a significant proportion of a wide variety of neoplasms. Using Northern blots or RT-PCR, Klenova et al. (2002) analyzed BORIS mRNA levels in over 200 cancer cell lines representing most of the major forms of human tumors and detected transcripts in more than one half of the cell lines tested. Subsequent analysis of primary cancers, for breast cancer samples, confirmed the results obtained with the cell lines.

SUMMARY OF THE INVENTION

The present invention is directed to nonfunctional mutant polynucleotides encoding the Brother of Regulator of Imprinted Sites (BORIS) tumor antigen and the use of such polynucleotides for preventive vaccination and immunotherapy of primary or metastatic cancer. The polynucleotide may be either DNA or RNA. In one preferred embodiment, the tumor antigen is a non-functional mutated form of the BORIS molecule lacking DNA binding capability. In another preferred embodiment at least one zinc finger (ZF) domain is nonfunctional due to mutation or deletion and the function of BORIS is eliminated. In another preferred embodiment any combination of the zinc finger domains are mutated or deleted and function of the BORIS protein, polypeptide or peptide is eliminated. In yet another preferred embodiment all of the ZF binding sites are deleted. In still another preferred embodiment the polynucleotide encoding the mutated form of BORIS is fused to a molecular adjuvant. In still another preferred embodiment the polynucleotide encoding the nonfunctional mutated form of BORIS is mixed with at least one other polynucleotide encoding a molecular adjuvant. Any molecular adjuvant that increases cellular immune response can be used. Cytokines, chemokines and co-stimulatory molecules are particularly preferred. Particularly preferred chemokines, cytokines and co-stimulatory molecules are beta-defensin2, IL12, IL18, MIPα3, IFNγ and CD80/86.

The present invention is also directed to a vector comprising a polynucleotide encoding a nonfunctional mutated form of BORIS. In a preferred embodiment the vector directs expression in a bacterial, mammalian, yeast cell or viral system.

The present invention is further directed to a nonfunctional modified (mutant) form of a BORIS protein, polypeptide or peptide. The nonfunctional mutant can be made using any method that introduces deletions, substitutions or additions in the sequence that result in a non-functional protein. In a preferred embodiment the mutant BORIS protein, polypeptide or peptide lacks DNA binding ability. In another preferred embodiment the mutant BORIS protein, polypeptide or peptide is mixed with conventional adjuvant. In yet another preferred embodiment the nonfunctional mutant BORIS protein, polypeptide, or peptide is attached to a. pharmaceutically acceptable carrier (backbone). In still another preferred embodiment the nonfunctional mutant BORIS protein, polypeptide or peptide is attached to a peptide that modifies BORIS and retains it antigenic property. In yet another preferred embodiment the nonfunctional mutant BORIS protein, polypeptide or peptide is attached to a protein transducing domain (PTD).

The present invention is also directed to dendritic cells expressing a nonfunctional mutant BORIS molecule. In a preferred embodiment the dendritic cells are transfected with DNA encoding a mutant BORIS molecule. In yet another preferred embodiment the dendritic cells are infected with a viral vector that encodes a nonfunctional mutant BORIS molecule. In yet another preferred embodiment the dendritic cells are loaded with nonfunctional mutant BORIS protein, polypeptide, peptide or any nonfunctional modified protein form of BORIS.

The present invention encompasses cellular immune responses generated against a nonfunctional mutant form of the BORIS protein, polypeptide, peptide or any nonfunctional modified protein form of BORIS. The present invention encompasses antibodies raised against a nonfunctional mutant form of the BORIS protein, polypeptide, peptide or any modified protein form of BORIS.

The present invention also encompasses a cancer preventive or therapeutic vaccine comprising a polynucleotide encoding a nonfunctional mutant form of BORIS, a nonfunctional mutant BORIS protein, polypeptide or peptide or dendritic cells expressing a nonfunctional mutant BORIS molecule.

The present invention is also directed towards a method of treating cancer comprising administering to a patient (prophylactic vaccine) in need thereof an effective amount of a polynucleotide encoding a nonfunctional mutant form of BORIS, a nonfunctional mutant BORIS protein, polypeptide or peptide, or dendritic cells expressing or containing a nonfunctional mutant BORIS molecule. Administration can be via an intramuscular, subcutaneous, intradermal, intravenous, nasal, rectal, vaginal or peritoneal route. The cancer can be a primary or metastatic cancer. The patient can have multiple different types of cancer. In a preferred embodiment the cancer is breast, prostate, ovarian, gastric, liver, endometrial, glioma, colon, or esophageal cancer.

BRIEF DESCRIPTION OF THE DRAWINGS

FIGS. 1a, b, and c present the results of vaccination of mice (n=10) with pBORIS (DNA immunization) pIL12/IL18 (molecular adjuvant). This resulted in protection of mice from challenge with $10^4$ 4T1 tumor cells naturally expressing mouse BORIS. FIG. 1a shows survival rate on the Y axis and Days after tumor challenge on the X axis for pBORIS/pIL12/IL18, pIL12/IL18 and vector only. FIG. 1b show the relationship between tumor volume and days after tumor challenge for pBORIS/pIL12/IL18, pIL12/IL18 and vector only. FIG. 1c shows the significant difference in tumor volume at day 21 between groups immunized with pBORIS/pIL12/IL18 vs. pIL12/IL18 and vector only (*P<0.001).

FIGS. 2a and b show the relationship between percent survival and days after tumor challenge (a) and tumor volume and days after challenge for mice vaccinated with pBORIS (DNA immunizations) followed by Ad5-BORIS (viral like particles) and challenged with $10^4$ 4T1 cells. Data demonstrated a full protection against the tumor challenge after al least 33 days of challenge.

FIG. 3a, b, c present the results of gene-gun immunization of mice with pBORIS plus pIFNγ or pIL12/IL18 followed by challenge with $10^5$ 4T1 tumor cells. FIG. 3a shows a prolonged time of tumor growth to the volume of 2 $cm^3$ and FIG. 3b shows a lower the tumor growth rate. FIG. 3c shows significant differences in tumor volume at day 14 between groups pBORIS/pIFNγ vs. vector (p<0.05), pBORIS/pIL12/IL18 vs. pIL12/IL18 (P<0.05) and pBORIS/pIL12/IL18 vs. vector (P<0.01).

FIGS. 4a, b, and c show the results of mice vaccinated with pBORIS (DNA immunization) followed by injection of Ad5-BORIS (viral like particles). FIG. 4a shows a significantly prolonged survival of the vaccinated mice while FIG. 4b shows that these mice had a lower the tumor growth rate and prolonged the time of tumor growth to the volume of 2 $cm^3$ after challenge of mice with $10^5$ 4T1 tumor cells. FIG. 4c shows a significant difference in tumor volume at day 15 between groups Ad5-BORIS vs. Ad5 (P<0.001).

FIG. 5 shows the best-fit alignment of the human (bottom sequence-SEQ ID NO: 2) and mouse (top sequence-SEQ ID NO: 4) BORIS polypeptides produced by the GCG-package of programs with zero-penalty for the gap extension with conserved zinc finger regions highlighted and indicated as ZF-11.

DETAILED DESCRIPTION OF THE INVENTION

Figure 6:
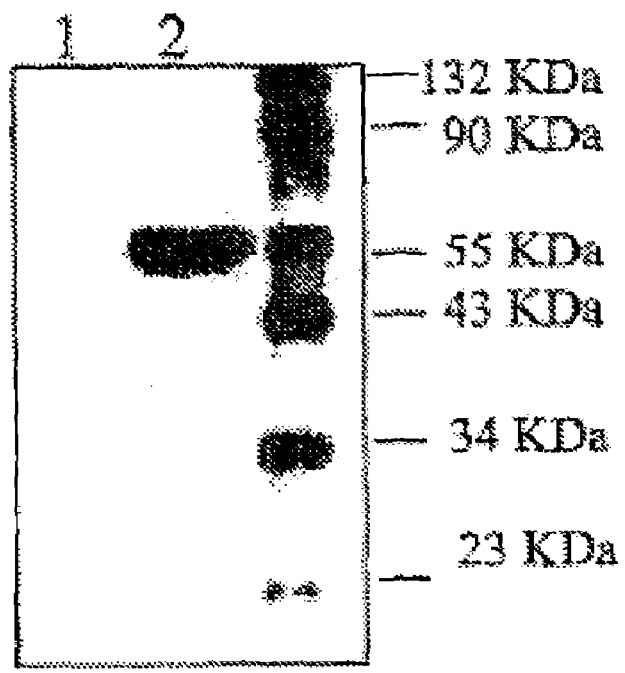
FIG. 6 shows detection of expression of pShuttle -BORIS in CHO by immunoblotting.

While the present invention may be embodied in many different forms, specific illustrative embodiments are disclosed herein that exemplify the principles of the invention. It should be emphasized that the present invention is not limited to the specific embodiments illustrated.

The present invention involves the use of an antigen expressed only in immune-privileged testis cells and appearing in many transformed tumor cells to prevent a tolerating effect, which may induce other tumor antigens. The invention also involves the introduction of specific changes in the DNA encoding the antigen to eliminate side effects and autoimmune reactions. In this context the following definitions apply.

The terms "tumor," "cancer," "neoplasm," "neoplasia" and their etymological relatives are used interchangeably in the context of this application to refer generally to dysproliferative diseases and the attendant affected cells or cell masses. Preferably, the dysproliferative cells referred to herein express an immune-privileged antigen.

Cytotoxic T lymphocytes (CTLs) are effector T cells, usually CD8+ that can mediate the lysis of target cells bearing antigenic peptides associated with a MHC molecule. Other cytotoxic cells include gamma/delta and CD4+ NK 1.1+ cells.

Immune privilege and immune-privileged antigen refer to the isolation of certain sites and antigens within the body from the immune system and thus relate to antigens to which an immune response is not normally developed. Immune-privileged antigens expressed ectopically (i.e., outside of their normally immune-privileged sites) may result in autoimmunity or tumor immunity. Immune-privileged antigens are expressed by some tumors resulting in an immune response to both the tumor and to non-tumor sites expressing the same immune-privileged antigens.

Antigen presenting cells (APCs) are cells including dendritic cells, macrophages, and B cells, that can process and present antigenic peptides in association with class I or class II MHC molecules and deliver a co-stimulatory signal necessary for T cell activation.

A "zinc finger domain" refers to a small independently folded domain that requires coordination of one or more zinc ions to stabilize its structure. Fingers bind to three base pair subsites and specific contacts are mediated by amino acids in positions-1, 2, 3 and 6 relative to the start of the alpha helix.

A "nonfunctional mutant form of BORIS" refers to a BORIS protein, polypeptide or peptide that lacks function. "Lack of function" is intended to mean failing to perform any one of the critical activities of the wildtype BORIS molecule such as DNA binding, re-establishment of the paternal DNA-methylation pattern, etc.

"Nonfunctional mutant" refers to changes at the DNA or amino acid level that destroy the wildtype activity of the resulting protein. Such changes can be amino acid substitutions, deletions or additions in areas of the molecule that act as catalytic sites and/or participate in binding DNA or protein. Examples of changes that are able to destroy activity are deletions or substitutions of critical amino acids participating in a catalytic or binding interaction, additions of amino acids that alter the required three dimensional structure of the site involved in catalytic and/or binding interactions, or additions or deletions of nucleotides that cause frame shifts, thus destroying the required three dimensional structure. Mutations can be produced using common molecular techniques such as PCR, use of oligonucleotides, etc. (for example see Sambrook, Maniatis and Fritsch). Naturally occurring mutations can also be isolated from cell populations (for example see Sambrook, Maniatis and Fritsch).

A "peptide" refers to a molecule containing at least 2 amino acids joined by a peptide bond. A "polypeptide" refers to a molecule containing at least 10 amino acids joined by peptide bonds and a "protein" refers to a molecule containing at least 20 amino acids.

A "polynucleotide encoding a nonfunctional mutant form of BORIS" refers to any polynucleotide having at least 50%, 60% or 70% sequence identity with the human (SEQ ID NO: 1) or mouse (SEQ ID NO: 3) BORIS polynucleotide, more likely 75%, 80%, 90%, 95% or 96%, 97%, 98% or 99% sequence identity with the human (SEQ ID NO: 1) or mouse (SEQ ID NO: 3) BORIS polynucleotide.

A "nonfunctional mutant BORIS peptide, polypeptide or protein" refers to a BORIS molecule that fails to perform any one of the critical activities of the wildtype BORIS molecule such as DNA binding, re-establishment of the paternal DNA-methylation pattern, etc. The "nonfunctional mutant BORIS peptide, polypeptide or protein" has at least 50%, 60% or 70% sequence identity with the human (SEQ ID NO: 1) or mouse (SEQ ID NO: 2) BORIS peptide, polypeptide or protein, more likely 75%, 80%, 90%, 95% or 96%, 97%, 98% or 99% sequence identity with the human (SEQ ID NO: 2) or mouse (SEQ ID NO: 4) BORIS peptide, polypeptide or protein.

A nonfunctional mutated BORIS molecule is recognized as a non-self antigen expressed only in transformed tumor cells and is used as an antigen to overcome the limitations of the prior art. The mutant form of BORIS is used as an ideal non-toxic vaccine, because it should not have any undesirable side effects caused by its DNA-binding activity and/or native function. In other words, the mutant BORIS used for vaccination has no functional activity and is present only as an immunogen (antigen). Unlike other tumor-specific antigens, BORIS is not expressed in the normal tissues in women. Furthermore, even though BORIS is expressed during the pubertal development of the normal testis in men, introduction and/or expression of a nonfunctional mutant BORIS should not be harmful, because the testis is an immune-privileged tissue (inaccessible for immune cells). In other words, the anti-BORIS immune response generated after immunization is not dangerous for normal cells and a BORIS vaccine does not induce autoimmunity. In addition, generation of a potent immune response is guaranteed because BORIS, unlike other tumor-specific antigens, is recognized as a foreign antigen. BORIS specific T cells are not deleted in thymus and recognize mutant BORIS as a non-self antigen and generate an immune response.

In one embodiment cDNA encoding mouse (mBORIS) BORIS is generated by RT-PCR on mRNA isolated from mouse or human testis. The DNA binding domain of the molecule is deleted and substituted with a small spacer known to work well in creating single chain Fv domain antibodies. The correct sequence is confirmed by automated nucleotide sequence analysis. The resulting molecule lacks the 11 ZF domains and consists of the N terminal region of mBORIS (amino acids 1-258) linked to the C terminal region (amino acids 573-636) through an 18-amino acid spacer.

The mutated cDNA is cloned into a pORF vector under control of the hEF1-HTLV promoter, however other expression vectors can be used. Here, the mutated cDNA is operably linked to a promoter and/or regulatory molecules that are capable of causing expression in the host cell. Viral vectors can be used including α-virus DNA or RNA vectors, adenoviruses and retroviruses (see Vasilevko, V. et al. (2003) *Clin. Exp. Metastas.* 20:489-98.; Leitner, W. W. et al. (2003) Nat Med 9:33-39; Ribas, A et al. (2002) Curr.Gene Ther 2:57-78).

In addition to the above, the invention encompasses using viral like particles encoding nonfunctional mutant BORIS molecules such as those from adenovirus, human hepatitis B, human hepatitis C, vaccinia virus, polyoviurs, etc. Recombinant viral proteins from different viruses have the useful property of self-assembling into virus-like particles (VLPs). These particles contain no viral nucleic acids and are therefore non-replicative, non-infectious and retain conformationally correct antigenic epitopes. VLP production has been shown in many experimental systems, such as mammalian cells, baculovirus-infected insect cells, yeasts, E. coli, cell free systems and transgenic plants. Importantly, vaccination with VLPs generates production of not only humoral but also cellular immune responses. VLPs infect professional APCs and subsequently induce protective cellular immune responses, including CD4+Th1 (type of CD4+T cells that helps CD8+T cells) and CD8+ CTL responses. Thus, VLPs have clearly revealed an exceptional capacity to activate cellular immune responses (T cell reponses). The potential use of VLPs as prophylactic vaccines is currently being assessed in a number of different clinical trials. Results from these trials have been encouraging with excellent tolerability and high immunogenicity reported in each trial. Generation of a VLPs vaccine composed of truncated BORIS antigen will promote the induction of strong cellular immune responses against cancer cells expressing this tumor associated antigen. Hepatitis B virus (HBV) core antigen (HBcAg) and VSV are examples of suitable VLPs.

To generate a more robust cellular immune response, the truncated or mutated mBORIS is fused with molecular adjuvants such as B7 costimulatory molecules, beta-defensin 2/3, MIP3α, IFNγ, cytokines, chemokines, etc. prior to cloning into the vector. Other suitable molecular adjuvants are listed in the Table below

| | |
|---|---|
| XCL1 (Lymphotactin α, SCM-1α, ATAC) | IL-1 α, IL-1β |
| XCL2 (Lymphotactin β, SCM-1β, ATAC) | IL-2 |
| CCL1 (I-309, TCA3) | IL-3 |
| CCL2 (MCP-1, MCAF, JE) | IL-4 |
| CCL3 (MIP-1, α MIP-1αS, LD78α) | IL-5 |
| LD78β (MIP-1αP) | IL-6 |
| LD78γ | IL-7 |
| CCL4 (MIP-1β) | IL-9 |
| CCL5 (RANTES) | IL-10 |
| CCL7 (MCP-3) | IL-11 |
| CCL8 (MCP-2) | IL-12 |
| CCL9 (MIP-1γ) | IL13 |
| CCL10 (CCF18) | IL14 |
| CCL11 (Eotaxin) | IL-15 |
| CCL12 (MCP-5) | IL-16 |
| CCL13 (MCP-4, CKβ10) | IL-17 |
| CCL15 (HCC-2, Lkn-1, MIP-5, CC-2, NCC-3, MIP-1δ) | IL-18 |
| CCL16 (NCC-4, LEC, HCC-4, LMC, Mtn-1, LCC-1, CKβ12) | IL-21 |
| CCL17 (TARC) | IL-23 |
| CCL18 (DC-CK1, PARC, MIP-4, AMAC-1, CKβ7) | TNFα |
| CCL19 (exodus-3, ELC, MIP-3β, CKβ11) | TNFβ |
| CCL20 (exodus-1, MIP-3α, LARC, ST38) | IFNα |
| CCL21 (exodus-2, SLC, 6-Ckine, TCA4, CKβ9) | IFNβ |
| CCL22 (MDC, ABCD-1, DC/B-CK) | IFNγ |
| CCL23 (MIP-3, MPIF-1, CKβ8-1) | M-CSF |
| CCL24 (MPIF-2, CKβ6, eotaxin-2) | G-CSF |
| CCL25 (TECK, Ckβ15) | GM-CSF |
| CCL26 (Eotaxin-3, MIP-4α) | MIF |
| CCL27 (ALP, Skinkine, ILC, ESkine, CTAK) | CD46 (MCP) |
| CXCL8 (IL-8) | CD27 (T14, S152) |
| CXCL9 (mig) | CD54 (ICAM-1) |
| CXCL10 (γIP-10, crg-2) | CD80 (B7-1, BB1) |
| CXCL11 (H174, β-R1, I-TAC, IP-9) | CD86 (B7-2, B70) |
| CXCL12 (SDF-1α, SDF-1β, PBSF) | CD134 (FLT3, STK-1) |
| CXCL13 (BLC, BCA-1) | CDw137 (4-1BB) |
| CXCL14 (BRAK, bolekine) | CDw150 (SLAM, IPO3) |
| CX₃CL1 (Fractalkine, neurotactin) | CD153 (CD30L) |
| Defensin (DFα, DFβ) | CD161 (NKR-P1A) |

Alternatively, conventional adjuvants can be used such as Tween 80, 5% ethanol and Bupivacaine for DNA immunization. Other examples of conventional adjuvants include mineral salts (such as aluminium hydroxide and aluminium phosphate gels), oil emulsions and surfactant based formulations such as MF59, QS21, AS08 [SBAS2] (oil-in-water emulsion+MPL+QS21), Montanide ISA-51 and ISA-720, particulate adjuvants such as virosomes, AS04 ([SBAS4] Al salt with MPL), ISCOMS, polylactide co-glycolide (PLG), microbial derivatives (natural and synthetic) including monophosphoryl lipid A (MPL), Detox (MPL+M.Phlei cell wall skeleton), AGP[RC-529], DC_Chol, OM-174 (lipid A derivative), CpG motifs, modified LT and CT (genetically modified bacterial toxins), endogenous immunomodulators such as GM-CSF, IL-12, Immudaptin, as well as all other chemokines, cytokines and costimulatory molecules listed in the table above and inert vehicles, such as gold particles.

Adjuvants can be either mixed with the polypeptide encoding a nonfunctional mutant form of the Brother of Regulator of Imprinted Sites (BORIS) protein, polypeptide or peptide, a nonfunctional mutant BORIS protein, polypeptide or peptide and a dendritic cell expressing a nonfunctional mutant BORIS peptide, polypeptide or protein Additional peptide molecules can be included in the nonfunctional mutant BORIS constructs to enhance/promote presentation of the nonfunctional mutant BORIS by the professional antigen presenting cells (APC) cells of the MHC class pathway. One example of this is a construct made with the protein transducing domain (PTD). In general, an immune response relies on native antigen processing and presentation. The tumor-associated antigens can be expressed in bacteria, yeast or mammalian cells, however protein antigens expressed in those systems likely will not maximally stimulate T cell responses (either CTL responses or Th1-biased responses) since the soluble exogenous proteins are processed mainly by the MHC class II pathway. In fact, many anti-tumor vaccines rely on the induction of CD8+ CTL, but this usually requires that the protein is synthesized within the cytosol of APC. Unfortunately, in general the plasma membranes of eukaryotic cells are impermeable to the majority of proteins. It has recently been shown, however, that foreign proteins fused with the protein transducing domain (PTD) can penetrate the plasma membrane, allowing the proteins to accumulate within the cells. This enhances the presentation of foreign peptides by the MHC class I molecules of APCs to the antigen-specific CD8+T cells.

Vaccination/Immunization

Vaccine formulations of the present invention comprise an immunogenic amount of a polynucleotide encoding a nonfunctional mutant BORIS protein, polypeptide or peptide, a nonfunctional mutant BORIS protein, polypeptide or peptide or a dendritic cell expressing a nonfunctional mutant BORIS protein, polypeptide or peptide in combination with a pharmaceutically acceptable carrier. Mimeotopes, which are polypeptides of unrelated sequence but with a 3-dimensional structure corresponding to the nonfunctional mutant BORIS protein, polypeptide or peptide and that immunologically function in an identical manner can be used. Mimeotopes, which are any biological molecule that is unrelated to BORIS structure, but has identical 3-d antigenic epitope/s and can be recognized by anti-BORIS T cells.

An "immunogenic amount" is an amount of the polypeptide encoding a nonfunctional mutant BORIS protein, polypeptide or peptide, nonfunctional mutant BORIS protein, polypeptide or peptide or a dendritic cell expressing a nonfunctional mutant BORIS protein, polypeptide or peptide sufficient to evoke an immune response in the subject to which the vaccine is administered The amount administered is an amount that induces a desired immune response, and the desired degree of protectionExemplary pharmaceutically acceptable carriers include, but are not limited to, sterile pyrogen-free water and sterile pyrogen-free physiological saline solution.

The vaccine formulations of the present invention are suitable for patients diagnosed with having at least one type of cancer including, but not limited to, breast, prostate, ovarian, gastric, liver, endometrial, glioma, colon, and esophageal cancer. The vaccine formulations of the present invention are also suitable for patients known to have a genetic susceptibility to cancer. In addition, the vaccine formulations of the present invention are suitable for the general population at large, including those without cancer or without a genetic susceptibility to cancer, who wish to invoke protection against contracting at least one type of cancer that expresses the wildtype BORIS protein, polypeptide or peptide.

Administration of the vaccine formulation may be carried out by any suitable means, including parenteral injection (such as intraperitoneal, subcutaneous, or intramuscular injection), intradermal, intravenous, nasal, rectal, vaginal or to an airway surface. Topical application of the virus to an airway surface can be carried out by intranasal administration (e.g. by use of dropper, swab, or inhaler which deposits a pharmaceutical formulation intranasally). Topical application of the virus to an airway surface can also be carried out by inhalation administration, such as by creating respirable particles of a pharmaceutical formulation (including both solid particles and liquid particles) containing the replicon as an aerosol suspension, and then causing the subject to inhale the respirable particles. Methods and apparatus for administering respirable particles of pharmaceutical formulations are well known, and any conventional technique can be employed. An "immunogenic amount" is an amount of the replicon particles sufficient to evoke an immune response in the subject to which the vaccine is administered.

When RNA or DNA is used as a vaccine, the RNA or DNA can be administered directly using techniques such as delivery on gold beads (gene gun), delivery by liposomes, or direct injection, among other methods known to people in the art. Any one or more constructs or replicating RNA can be use in any combination effective to elicit an immunogenic response in a subject. Generally, the nucleic acid vaccine administered may be in an amount that will induce a desired immune response, and the degree of protection desired. Precise amounts of the vaccine to be administered may depend on the judgment of the practitioner and may be peculiar to each subject and antigen.

The vaccine may be given in a single dose schedule, or preferably a multiple dose schedule in which a primary course of vaccination may be with 1-10 separate doses, followed by other doses given at subsequent time intervals required to maintain and or reinforce the immune response, for example, at 1-4 months for a second dose, and if needed, a subsequent dose(s) after several months. Examples of suitable immunization schedules include: (i) 0, 1 months and 6 months, (ii) 0, 7 days and 1 month, (iii) 0 and 1 month, (iv) 0 and 6 months, or other schedules sufficient to elicit the desired immune responses expected to confer protective immunity, or reduce disease symptoms, or reduce severity of disease.

Human (hBORIS) can be isolated from human testis and manipulated in the same manner. Likewise, BORIS can be isolated from the testis of any mammal or vertebrate and used similarly.

EXAMPLES

1. Generation of a Plasmid Encoding the ZF Deleted Form of the mBORIS Molecule Under the hEF1-HTLV Promoter An RT-PCR reaction is performed using poly-A RNA from mouse testis and the following primers:

```
MB1F                                          (SEQ ID NO: 5)
5'-CGTCACCATGGCTGCCGCTGAGGTCCCTG

MB1R                                          (SEQ ID NO: 6)
5'-AAGCTTCTGAAAGCTCTGAGGCTTTCCCTTGG

MB2F                                          (SEQ ID NO: 7)
5'-GGATCCGAGACGTTAGCCCCCAACAAGGACAGG

MB2R                                          (SEQ ID NO: 8)
5'-GAATTCTCACTTATCCATCATGTTAAAGATCATCTCGCAGG

SpF                                           (SEQ ID NO: 9)
5'-AGCTTGGTGGAGGCGGTTCAGGCGGAGGTGGCTCTGGCGGTGGCGGA
TCGG

SpR                                          (SEQ ID NO: 10)
5'-GATCCCGATCCGCCACCGCCAGAGCCACCTCCGCCTGAACCGCCTCC
ACCA
```

The PCR conditions are: 94° C. for 30 s, 60° C. for 30 s, 72° C. for 2 mm Thirty (30) cycles are performed.

The PCR products are subcloned into the PCRII-TOPO cloning vector (Invitrogen). The C-terminal cDNA in PCRII-TOPO is restricted with BamHI enzyme and positive clones containing the insert are pooled and subsequently restricted with HindIII enzyme. Spacer primers (SpF and SpR) are annealed to create overhanging sticky ends and ligated into the BamHI-HindIII restricted vector. The N-terminal encoded fragment is restricted with HindIII and the inserts which are now separated from the vector are pooled and ligated into a HindIII digested construct containing the C-terminus and spacer. Clones with the proper orientation are then selected, sequenced (see, for example, the sequence for the ZF deleted BORIS molecule below) and subcloned into the pORF plasmid under control of the hEF1-HTLV promoter (Invivogen).

CHO cells are transfected with the resulting construct using standard molecular techniques (Sambrook J, Fritsch E F and Maniatis T (1989) Molecular Cloning: A Laboratory Manual, Cold Spring Harbor; incorporated herein by reference)

The expression of the zinc finger deleted mBORIS construct is analyzed by Northern blots of mRNA isolated from transfected CHO cells using standard molecular technique (Sambrook et al., 1989).

2. Immunization of Mice with DNA Encoding the ZF Deleted Form of the Boris Molecule.

The plasmid encoding the ZF deleted mBORIS construct is isolated using the EndoFree Plasmid maxi kit (Qiagen). Purity of the plasmid DNA was confirmed by UV spectrophotometry (260 nm/280 nm absorbance ratio>1.7) and gel electrophoresis.

Gold beads are coated with DNA (1 μg/0.5 mg gold) and 5-7 weeks old Balb/c mice are immunized using the Helios Gene Gun. Mice are boosted in the same way, three times bi-weekly Ten days after the last boost, the mice are bled and challenged with $1.0 \times 10^4$ or $1.0 \times 10^5$ 4T1 breast cancer cells. The tumor size is measured everyday or every two-three sing calipers.

3. Protective Studies

Immunization of Mice with Plasmid Vaccine:

One example of a preventive anti-cancer vaccine approach is the use of DNA encoding a deleted form of the mouse BORIS molecule that lacks the zinc finger domains and therefore the DNA binding property.

Purified plasmid is used to coat gold beads (2 μg plasmid/ 0.5 mg gold particles) as was we described earlier (Ghochikyan et al.(2003) Eur J Immunol 33:3232-41). Immunizations of BALB/c mice with plasmid is performed on shaved abdominal skin using the Helios gene gun(Bio-Rad, Hercules, Calif.) as described by Ross et al. (2000, Nat. Immunol 1:127-131). Briefly, mice are bombarded 3 times with doses containing 2 μg of DNA per 0.5 mg of ~1 μm gold beads (DeGussa-Huls Corp., Ridefield Park, N.J.) at a helium pressure setting of 400 psi. Mice are immunized and boosted by the same method biweekly and challenged with two different doses of 4T1 breast cancer cells ($10^5$ or $10^4$) ten days after the last boost as described (Vasilevko et al., 2003). Different groups of mice are immunized with plasmid encoding a modified BORIS molecule mixed with DNA encoding a certain molecular adjuvant(s) (see Table 1 for details). Such molecular adjuvants are known to increase cellular immune responses to the different antigens.

TABLE 1

Mice were immunized five times biweekly using a BORIS protective vaccine (pORF-mBORIS) mixed with pORF-mGMCSF (encoding mouse GMCSF), pORF-mIFNγ (encoding mouse IFNγ), or pORF-mIL12 + pIRES-mIL18 (two plasmids encoding mouse IL12 and IL18, accordingly). After the last boost, mice are challenged with $10^5$ or $10^4$ 4T1 mouse breast cancer cells that expressed the modified BORIS molecule.

| Groups | Immunogen | Molecular Adjuvant | Challenge with 4T1 cells |
|---|---|---|---|
| 1 | pBORIS | pGM-CSF | $10^5$ |
| 2 | pBORIS | pIFNγ | $10^5$ |
| 3 | pBORIS | pIL12/IL18 | $10^5$ |
| 4 | Vector | — | $10^5$ |
| 5 | — | pIL12/IL18 | $10^5$ |
| 6 | pBORIS | pIL12/IL18 | $10^4$ |
| 7 | Vector | — | $10^4$ |
| 8 | — | pIL12/IL18 | $10^4$ |

Generation of Adenoviral Vector Encoding the ZF Deleted Form of Mouse BORIS Molecule (Ads-BORIS) and Immunization of Mice Ad5-BORIS recombinant adenovirus is prepared using AdEasy XL Adenoviral Vector System from Stratagene. The shuttle vector is constructed by subcloning the ZF-deleted mBORIS fragment into the plasmid pShuttle-CMV. For this purpose the BORIS fragment is synthesized by PCR using pORF-mBORIS plasmid as a template and the following primers:

SalI-MB-F                                    (SEQ ID NO: 11)
5'-ACGCGTCGACATGGCTGCCGCTGAGGTCCCTGTCCCTTCTGGG

NotI-MB-R                                    (SEQ ID NO: 12)
5'-CGGCCGTCACTTATCCATCATGTTAAAGATCATCTCGCAGG

The PCR product is subcloned into the PCR4-TOPO cloning vector (Invitrogen). BORIS fragment is restricted using SalI and NotI restriction endonucleases. The resulting product is purified on an agarose gel and subcloned using SalI-NotI cloning sites into the pShuttle-CMV vector.

The in vitro expression of ZF-deleted mBORIS is analyzed in CHO cells by immunoblotting as shown in FIG. 6.

The shuttle vector carrying the deleted BORIS is linearized with PmeI and purified on an agarose gel. Electroporation competent cells BJ-5183-Ad-1 are transformed with Pme-digested pShuttle-mBORIS plasmid to produce the recombinant Ad plasmid. AD-293 cells are transfected with selected recombinant Ad-BORIS DNA and primary viral stocks are prepared. The primary viral stock resulting ($10^7$ pfu/ml) is amplified in AD-293 cells and then purified on a CsCl gradient. The purified virus is dialyzed against PBS-5% sucrose and used for immunization of mice.

Balb/c mice immunized with pBORIS four times biweekly boosted once. i.m. with Ad5-BORIS ($10^9$ PFU). Control animals injected with vectors are boosted with Ad5. Ten days after the last boost mice are challenged with two different doses of 4T1 breast cancer cells ($10^5$ and $10^4$) as described (Vasilevko et al., 2003).

Tumor Cell Lines

Mammary tumor cell lines provided by Dr. F. Miller (Karmanos Cancer Institute, Detroit, Mich.) are used. 4T1.2 cells are a thioguanine-resistant variant derived from 410.4 cells (a mammary tumor cell line originally isolated from a single spontaneously arising mammary tumor in a BALB/c fC3H mouse) without mutagen treatment. The cells are cultured (37° C., 10% $CO_2$) in Dulbecco-modified Eagle's essential medium (DMEM) containing low glucose and supplemented with 5% fetal bovine serum, 5% newborn calf serum, 2 mM glutamine, 100 units/ml penicillin, 100 μg/ml streptomycin, 0.1 mM non-essential amino acids and 1 mM sodium pyruvate (D10) (Life Technologies, Inc.).

Determination of Tumor Volumes

Tumor volumes are determined daily by two-dimensional measurement and calculation using the formula $L \times (W^2)/2$, where L represents the length and W the width of the tumor. The experiments are terminated when the mouse appears moribund or the tumor reaches approximately 1.5 $cm^3$ for experiments involving a challenge with $10^4$ cells and 2 $cm^3$ for experiments involving a challenge with $10^5$ 4T1 cells.

The time of appearance (latency period) is designated as the time elapsed before a tumor with a volume in excess of 0.1 $cm^3$ is present. To determine tumor growth rate, scatter plots are analyzed in the near linear periods of tumor growth.

Statistical Analysis

Results on the average times of appearance of tumor nodules (latency period) and growth of tumor (tumor volume), as well as survival times are examined using an analysis of variance (ANOVA) and Tukey multiple comparisons post-test. Mean and standard deviation (SD) is calculated using GraphPad Prism 3.0 Software.

4. Immunology

B and T cell immune responses against BORIS are analyzed using two different immunization protocols.

1. Preparation of Mouse BORIS Proteins and Immunization of Mice.

Figure 7:
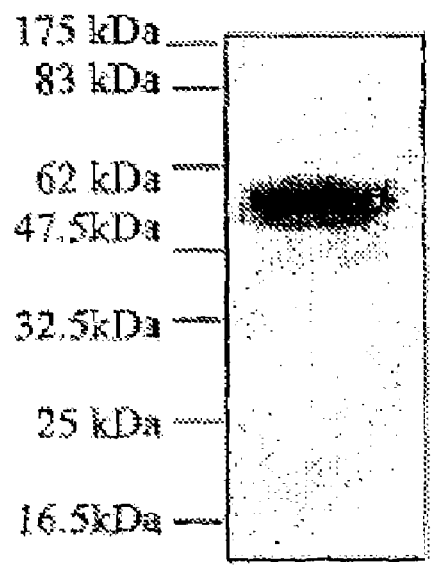
FIG. 7 shows purification of ZF-deleted BORIS from E.coli BL21(DE3). Protein is analyzed by 10% SDS-PAGE. The same data (not shown) is generated with BORIS fused with PTD

The ZF-deleted fragment of mouse BORIS is subcloned into the bacterial expression vector pET24d(+) by using NcoI-XhoI cloning sites in frame with a C-terminal 6His tag. Both sites are introduced and a stop codon is removed during the PCR step of cloning. In addition, plasmids encoding the deleted BORIS molecule fused with a Protein Transduction Domain (PTD) are constructed. The HIV-Tat protein transduction domain (Tat.$_{47\_57}$YGRKKRRQRRR) (SEQ ID NO: 13) is fused to the N-terminal end of the deleted BORIS via PCR and then cloned into the pET24d(+) vector NcoI-XhoI cloning sites. An *E.coli* BL21(DE3) strain transformed with the resultant pET-mBORIS or pET-TATmBORIS plasmids, is grown in LB with kanamycin at 28° C. until an $A_{600}$ 0.8 is reached. Protein synthesis is induced by the addition of IPTG at a final concentration of 1 mM. The cells are harvested three to five hours later by centrifugation and used for protein purification by affinity chromatography on a nickel-NTA (nitrilotriacetic acid) column (Qiagen), as illustrated in FIG. 7.

In addition, the ZF-deleted fragment of BORIS fused with PTD is subcloned into the yeast expression vector pGAPZalpha in frame with signal sequence into EcoRI-XbaI cloning sites. Both sites are introduced and the ATG initiation codon is removed during the PCR step of cloning. *Pichia pastoris* X33 strain is transformed by electroporation with pGAPZ-BORIS linearized with the AvrII restriction enzyme and positive clones are selected on YPD media containing 100 µg/ml Zeocin. For expression analysis, selected positive clones are grown in YPD/Zeocin broth and expression analyzed in supernatant at different time points by immunoblotting.

2. Immunization of Mice with Dendritic Cells (DC).

Primary bone marrow DCs are obtained from mouse bone marrow precursors as follows. Erythrocyte-depleted murine bone marrow cells harvested from femurs and tibias are plated in completed RPMI-10 media supplemented with recombinant murine GM-CSF (100 U/ml). On day 3, nonadherent granulocytes are gently removed and fresh media is added. Nonadherent DC are harvested at day 7 and purified by positive selection kit (Miltenyi) using CD11c Microbeads.

DC harvested at day 7 of culture and purified by positive selection are infected with Ad5-BORIS by incubation at $10^7$ cells/ml in RPMI 1640 at a multiplicity of infection of 1000-2000. After 1 h, complete medium is added to dilute the DC to a final concentration of $1\times10^6$ to $2\times10^6$ cells/ml. Cells are harvested 24 h later, extensively washed in order to discard any carryover of adenoviral particles, and used for immunization. In addition, DC that are harvested at day 7 of culture and purified by positive selection are incubated with 10 µg/ml ZF-deleted mBORIS protein at 37° C., 5% $CO_2$ for 24 hours, washed twice with PBS. Protein uptake by DC is analyzed in aliquots by Flow cytometry using anti-mouse BORIS antibodies and appropriate secondary antibodies labeled with FITC. Balb/c mice are immunized i.p. three times every three weeks with $1\times10^6$ DC and T cell responses are analyzed 10 days after the last boost in the cultures of splenocytes culture.

5. Results

Immunization results are presented in FIGS. 1-4.

DNA encoding a mutant form of the cancer-specific mouse BORIS antigen lacking DNA-binding function (deleted 11-Zinc Fingers) was constructed using the mammalian expression vectors pORF (Invivogen) and the AdEasy XL Adenoviral Vector System (Stratagene). These vaccines have been used as a prophylactic anti-cancer vaccine in a mouse breast cancer model. In this model we used BALB/c mice (H-2d haplotype) and the 4T1 native mammary tumor cell line, which is a thioguanine-resistant variant derived from 410.4 cells without mutagen treatment. Importantly, these mouse breast cancer cells are expressing the full mouse BORIS molecule as we demonstrated by RT-PCR. Therefore this is an ideal model for examination of ability of the BORIS molecule to be used as a protective cancer vaccine.

Two different types of experiments were conducted. The first type of experiments included a group of mice that were vaccinated with pBORIS (plasmid encoding deleted mouse BORIS molecule) mixed with DNA encoding different mouse cytokines (pGM-CSF; pIL12/IL18; pIFNγ) as molecular adjuvants. Mice were injected with vector (pORF) or pIL12/IL18 as controls. Mice were immunized and boosted using a gene gun technique and then were challenged with $10^4$ or $10^5$ 4T1 cells.

The second type of experiment included a group of mice that were vaccinated with pBORIS and boosted with replication defective adenoviral vector (Ad5) that was modified to express the ZF deleted mouse BORIS molecule (Ad5-BORIS). A group of mice injected with vector and boosted with Ad5 was used as a control. The animals were challenged with $10^4$ or $10^5$ 4T1 cells and tumor appearance and growth were analyzed. We note that it had previously been found that injection of as few as $10^4$ 4T1.2 cells into the mammary glands of BALB/c mice resulted in local growth of mammary tumors in 100% of challenged animals.

Vaccination with pBORIS plus pIL12/IL18 or pBORIS followed by Ad5-BORIS resulted in protection of mice from challenge with $10^4$ unmodified 4T1 tumor cells. Although 50% of the mice from the group immunized with pBORIS mixed with pIL12/IL18 generated small tumors (0.2-0.4 $cm^3$), they all survived by day 39. All experimental mice died approximate 10 days earlier.

The results for mice vaccinated with Ad5-BORIS were more extreme. On day 24, when mice in the control groups died from tumor growth, 100% of the mice immunized with the Ad5-BORIS vaccine were not only alive, but did not generate tumors at all. In fact they did not generate tumors at least till day 33 after the challenge. These results indicate that the ZF deleted BORIS vaccine effectively protected animals from a challenge with $10^4$ mammary tumor cells.

A second set of experiments was conducted using more stringent conditions and challenging mice with $10^5$ 4T1 tumor cells. Vaccination with the plasmid pBORIS plus pIFNγ or pIL12/IL18 significantly prolonged the time of tumor growth to a volume of 2 $cm^3$ and increased the survival of the BALB/c mice. The vaccination also lowered the tumor growth rate in mice that were challenged with $10^5$ 4T1 tumor cells. A more profound effect was detected in mice vaccinated with pBORIS and boosted with Ad5-BORIS before challenge with $10^5$ unmodified 4T1 cells. Here, on day 23, when all mice in the control group had died from tumor growth, 80% of the mice immunized with Ad5-BORIS were alive and surviving animals had significantly smaller sized tumors.

Separate groups of BALB/c mice were immunized with deleted mouse BORIS protein purified from *E.coli* system. Here, five mice were injected subcutaneously with protein (50 ug/mouse) mixed with Quil A Th1-type conventional adjuvant (Sigma). After 4 immunizations all animals induced significant titer of anti-BORIS antibodies. Another group of 5 mice were simultaneously immunized i/p with isolated dendritic cells infected with Ad5-BORIS. After 3 injections, the mice generated T cell responses against mBORIS that were detected in vitro in the culture of splenocytes activated with mBORIS protein. Therefore, immunization with BORIS induces B and T cell immune responses in mice and these immune responses are protecting the animal from challenge.

6. Truncated BORIS Attached to the PTD as a Subunit Vaccine.

A PTD is attached to a nonfunctional truncated or mutant BORIS protein and the fusion product generated in a yeast expression system. Genes encoding PTD and a nonfunctional mutant BORIS are subcloned into a yeast expression vector such as pGAPZα. The expressed and secreted protein is purified using standard molecular techniques. Mice are immunized with the antigen formulated in two different conventional adjuvants and immune responses as well as protection to the tumor antigen analyzed.

7. Virus-Like Particles Encoding a Nonfunctional Mutant BORIS as a Subunit Vaccine A VLP-BORIS subunit vaccine based on Hepatitis B virus (HBV) core antigen (HBcAg) is generated. This antigen self-assembles into VLPs after expression in yeast cells. Foreign sequences can be inserted into several regions of the HBcAg without disrupting the assembly process. Accordingly, a chimeric HBcAg-BORIS particle is generated that is used for immunization of mice.

8. Analysis in BALB/c and p53 KO Mice

Immune responses in BALB/c mice without challenge and in young p53 knockout mice that are not developing tumors in that age are analyzed. Both humoral and cellular immune responses in mice immunized with different BORIS vaccines are determined. Sera from immunized mice is analyzed for detection of anti-BORIS antibody production during a 3 month experimental period. CD4+ and CD8+ T cell proliferation and activation of T regulatory cells before and after the challenge of BALB/c mice is determined. Simultaneously, activation of NK cells that could directly kill mammary tumor cells is analyzed. Functional activity of BORIS-specific cytotoxic T lymphocytes (CTL) before and after challenge with mammary tumor 4T1 cells is demonstrated. P815 tumor cells that naturally express wildtype BORIS molecules are used as target cells along with 4T1 cells for detection of NK and CTL activity

ADDITIONAL REFERENCES

Filippova, G. N. et al. Tumor-associated Zinc Finger Mutations in the CTCF Transcription Factor Selectively Alter Its DNA-binding Specificity. *Cancer Research* 62:48-52 (2002).

Kim, J. J. et al. In vivo engineering of a cellular immune response by coadministration of IL-12 expression vector with a DNA immunogen. *J. Immunol* 158:816-826 (1997). Kim, J. J. et al. CD8 positive T cells influence antigen-specific immune responses through the expression of chemokines. *Journal of Clinical Investigation* 102:1112-24 (1998).

Kim, J. J. et al. Modulation of amplitude and direction of in vivo immune responses by co-administration of cytokine gene expression cassettes with DNA immunogens. *European Journal of Immunology* 28:1089-1103. (1998).

Kim, J. J. et al. Intracellular adhesion molecule-1 modulates beta-chemokines and directly costimulates T cells in vivo. *Journal of Clinical Investigation* 103:869-77 (1999).

Kim, J. J. et al. Macrophage Colony-Stimulating Factor Can Modulate Immune Responses and Attract Dendritic Cells in Vivo. *Human Gene Therapy* 11:305-321 (2000).

Lutz, M. B. et al. An advanced culture method for generating large quantities of highly pure dendritic cells from mouse bone marrow. *Immunol. Meth.* 223:77-92 (1999).

Nardelli, B. & Tam, J. P. The MAP system. A flexible and unambiguous vaccine design of branched peptides. *Pharm Biotechnol.* 6:803-819 (1995).

Resko, J. E. J. et al. Cell Growth Inhibition by the Multivalent Transcription Factor CTCF. *Cancer Research* 61:6002-7 (2001).

Ribas, A., Butterfield, L. H., Glaspy, J. A. & Economou, J. S. Cancer Immunotherapy Using Gene-modified Dendritic Cells. *Curr. Gene Ther* 2:57-78 (2002).

Ross, R. M., Xu, Y., Bright, R. A. & Robinson, H. L. C3d enhancement of antibodies to hemagglutinin accelerates protection against influenza virus challenge. *Nat. Immunol.* 1, 127-131 (2000).

Smith, M., Burchell, J. M., Graham, R., E. P., C. & J., T.-P. Expression of B7.1 in a MUC1-expressing mouse mammary epithelial tumour cell line inhibits tumorigenicity but does not induce autoimmunity in MUC1 transgenic mice. *Immunol.* 97, 648-655 (1999).

The invention being thus described, it will be apparent to one of ordinary skill in the art that various modifications of the materials and methods for practicing the invention can be made. Such modifications are to be considered within the scope of the invention as defined by the following claims.

Each of the references from the patent and periodical literature cited herein is hereby expressly incorporated in its entirety by such citation.

Sequence description: nucleotide sequence of ZF deleted BORIS molecule (SEQ ID NO: 14)

```
atg gct gcc gct gag gtc cct gtc cct tct ggg tac
ttc acc cag atc aaa gag cag aag ttg aag cct gga
gac cta gag gag gag aaa gag gag gac ggg gta caa
aga gtg gaa gcc cag gag gga gtt gtc aag gag gtg
gag gcc gag aac agt tgc ctg ctt ctg gag gcc agg
gcc ccg gtg gag agc gac agg cgg atc ctg acc ctg
caa acg gtg cac ctg gag tcc cag gat gtg cac cta
cag ggg ctg gga tgg ctg agc gtg cca cac tct gag
gag ctt tca ggg acg gta cca gag gcg gaa ggc ata
ctg cag ttg cca tcc gtg ctg tgg ctc gac cca gag
ccc cag ctc agc ctt cag cat tgc gtg acg gtc agc
atc ccg gaa gag ctg tac cca gag gag ctg cag
cgg ata cat ttt cac ctg ctg aga gag aat gtg cta
atg gcc gag gag aac cca gag tta aca cca gac ttg
gac gaa agc aca gcc ctg aaa aag ccc gaa gaa gat
gaa aag gac cag ctc ccg ccc cag gga gag aca gac
aag aga gaa gag agg ttg ctc ctt ctg gaa atg aaa
cca aaa gag gga aaa gac gac gaa att gtc ctg acc
att tcc cat cta agc ctc gaa gaa cag caa gat cca
cca gcg gcc aat cag aca agt gtg ccg gga gcc aaa
gcc gca aaa cca aaa cgg cgg agg cag acc aag gga
aag cct cag agc ttt cag aag ctt ggt gga ggc ggt
```

-continued
```
tca ggc gga ggt ggc tct ggc ggt ggc gga tcg gga
tcc gag acg tta gcc ccc aac aag gac agg aga cca
gtg aca agg aca cag gcc tcg gag gga gaa gca gga
cac aag gaa ggg gag cct cag tgc cct ggg gag cag
```

-continued
```
gct ctg ggc cac caa gga gaa gca gcg ggg agc cag
agc cca gac cac ggc ctt acc tgc gag atg atc ttt
aac atg atg gat aag tga
```

Sequence description: wildtype nucleotide sequence of mouse BORIS (SEQ ID NO: 3)

```
CCATTTTGTGCACCTTGATCAAAGCCCATGTCTACTAGGCCCCAGCACCTCTGCACCCCA
TAAAGATTGCACGCTCTTTTTCCATCAGGGGTCGTCACCATGGCTGCCGCTGAGGTCCCT
GTCCCTTCTGGGTACTTCACCCAGATCAAAGAGCAGAAGTTGAAGCCTGGAGACCTAGAG
GAGGAGAAAGAGGAGGACGGGGTACAAAGAGTGGAAGCCCAGGAGGGAGTTGTCAAGGAG
GTGGAGGCCGAGAACAGTTGCCTGCTTCTGGAGGCCAGGGCCCCGGTGGAGAGCGACAGG
CGGATCCTGACCCTGCAAACGGTGCACCTGGAGTCCCAGGATGTGCACCTACAGGGGCTG
GGATGGCTGAGCGTGCCACACTCTGAGGAGCTTTCAGGGACGGTACCAGAGGCGGAAGGC
ATACTGCAGTTGCCATCCGTGCTGTGGCTCGACCCAGAGCCCCAGCTCAGCCTTCAGCAT
TGCGTGACGGTCAGCATCCCGGAAGAGCTGTACCCACCAGAGGAGCTGCAGCGGATACAT
TTTCACCTGCTGAGAGAGAATGTGCTAATGGCCGAGGAGAACCCAGAGTTAACACCAGAC
TTGGACGAAAGCACAGCCCTGAAAAAGCCCGAAGAAGATGAAAAGGACCAGCTCCCGCCC
CAGGGAGAGACAGACAAGAGAGAAGAGAGGTTGCTCCTTCTGGAAATGAAACCAAAGAG
GGAAAAGACGACGAAATTGTCCTGACCATTTCCCATCTAAGCCTCGAAGAACAGCAAGAT
CCACCAGCGGCCAATCAGACAAGTGTGCCGGGAGCCAAAGCCGCAAAACCAAAACGGCGG
AGGCAGACCAAGGGAAAGCCTCAGAGCTTTCAGTGTGACACCTGCCCGTTCACTTCCTCC
AAGCTCTCAACTTTCAATCGTCACATCAAAATTCACAGCAATGAGAGGCCACACCTGTGT
CACCTGTGCCTGAAGGCCTTCCGGACTGTCACTCTTCTTAGGAACCATGTGAACACCCAC
ACAGGAACCAGGCCCCACAAGTGCAGGGACTGCGACATGGCGTTTGTCACCAGCGGAGAA
CTCGTCCGGCACAGGCGTTACAAACACACTTATGAGAAGCCCTTCAAGTGCTCCCTGTGC
AAGTACGCCAGCGTCGAGGCAAGCAAGATGAAGCGTCACATCCGCTCACACACGGGTGAG
CGTCCCTTCCAGTGTTGCCAGTGTGCTTATGCCAGCAGGGACTCCTACAAGCTGAAGCGC
CACATGAGGACACACTCAGGTGAGAAGCCGTATGAATGTCCCACCTGTCACGTCCGGTTC
ACCCAGAGCGGGACCATGAAAATCCATATAGCACAGAAGCACGGAGAGAATGTGCCCAAA
TACGAGTGTCCCCAGTGTGCCACCATCATCGCGAGGAAGAGCGACCTGCGTGTCCATCTG
CGTAACCTGCACAGCCAGAGCCCGGAGGAGATGAAGTGCCGATACTGTCCCGCTGGCTTC
CATGAGCGCTATGCCCTCATTCAGCACCAGAGGACCCACAAGAACGAGAAGAAGTTCAAG
TGCAAGCAGTGCGATTACGCGTGCAAGCAGGAGCGATGCTTGAAGGCGCACATGCGCATG
CACACAGGAGAAGCCCTTCTCCTGCCTGGCCTGCAACAAGCACTTCCGACAGAAGCAG
CTACTGACCGTGCACCTGAGGAAGTACCATGACCCGAACTTCGTCCCAATCTGCACCTG
TGCCTCAAGTGTGATAAACGTTTCTCCCGCTGGAGTAACCTGCAGAGACACAGAAAGAAG
TGTGACCCGGAGCATGAGACGTTAGCCCCCAACAAGGACAGGAGACCAGTGACAAGGACA
CAGGCCTCGGAGGGAGAAGCAGGACACAAGGAAGGGGAGCCTCAGTGCCCTGGGGAGCAG
GCTCTGGGCCACCAAGGAGAAGCAGCGGGGAGCCAGAGCCCAGACCACGGCCTTACCTGC
GAGATGATCTTTAACATGATGGATAAGTGATGGATAAGTGAGCAGTCGTGCCTCTCCGTG
```

-continued

```
CAGTGGCCTCTGGGGGAAGAAACCAGTTAGAAATAAGTTCCCAGACACAGCACAGTGTTC
TCAGAGTTTGAGATAGTGTGTAGAAATGTTTGAGAGAAGGGGAAAAAAACCCTGCAGCTA
TTTCCAAAGACTTGAGTCAGAGCTCGAAGTGAAGGTGCACATATCTGGGCCCTAGCAGGT
GCCCAGAATGAGTCAGGGACAGATTCTAGGTGATACTTATGTCCACGGGGGCTCAGACCA
GTTAACGCCTTGGTGGTCAGAGCAGAAAATTTTTTGAGTTGTTGTACCCACCCTCAA
```

Sequence description: wildtype nucleotide sequence of human BORIS (SEQ ID NO: 1)

```
   1 ggcaccagac gcggtgcacg aggcagagcc acaagccaaa gacggagtgg gccgagcatt
  61 ccggccacgc cttccgcggc caagtcatta tggcagccac tgagatctct gtcctttctg
 121 agcaattcac caagatcaaa gaactcgagt tgatgccgga aaaaggccta aggaggagg
 181 aaaaagacgg agtgtgcaga gagaaagacc atcggagccc tagtgagttg gaggccgagc
 241 gtacctctgg ggccttccag gacagcgtcc tggaggaaga agtggagctg gtgctggccc
 301 cctcggagga gagcgagaag tacatcctga ccctgcagac ggtgcacttc acttctgaag
 361 ctgtggagtt gcaggatatg agcttgctga gcatacagca gcaagaaggg gtgcaggtgg
 421 tggtgcaaca gcctggccct gggttgctgt ggcttgagga agggccccgg cagagcctgc
 481 agcagtgtgt ggccattagt atccagcaag agctgtactc cccgcaagag atggaggtgt
 541 tgcagttcca cgctctagag gagaatgtga tggtggccag tgaagacagt aagttagcgg
 601 tgagcctggc tgaaactgct ggactgatca agctcgagga agagcaggag aagaaccagt
 661 tattggctga agaacaaag gagcagctct ttttgtgga acaatgtca ggagatgaaa
 721 gaagtgacga aattgttctc acagtttcaa attcaaatgt ggaagaacaa gaggatcaac
 781 ctacagctgg tcaagcagat gctgaaaagg ccaaatctac aaaaaatcaa agaaagacaa
 841 agggagcaaa aggaaccttc cactgtgatg tctgcatgtt cacctcttct agaatgtcaa
 901 gttttaatcg tcatatgaaa actcacacca gtgagaagcc tcacctgtgt cacctctgcc
 961 tgaaaacctt ccgtacggtc actctgctgc ggaaccatgt taacacccac acaggaacca
1021 ggccctacaa gtgtaacgac tgcaacatgg catttgtcac cagtggagaa ctcgtccgac
1081 acaggcgcta taaacatact catgagaaac cctttaaatg ttccatgtgc aagtatgcca
1141 gtgtggaggc aagtaaattg aagcgccatg tccgatccca cactggggag cgccccttc
1201 agtgttgcca gtgcagctat gccagcagag atacctacaa gctgaaacgc cacatgagaa
1261 cgcactcagg tgagaagcct tacgaatgcc acatctgcca cacccgcttc acccagagcg
1321 ggaccatgaa aatacatatt ctgcagaaac acggcgaaaa tgtccccaaa taccagtgtc
1381 cccattgtgc caccatcatt gcacggaaaa gcgacctacg tgtgcatatg cgcaacttgc
1441 atgcttacag cgctgcagag ctgaaatgcc gctactgttc tgctgtcttc catgaacgct
1501 atgccctcat tcagcaccag aaaactcata agaatgagaa gaggttcaag tgcaaacact
1561 gcagttatgc ctgcaagcag gaacgtcata tgaccgctca cattcgtacc cacactggag
1621 agaaaccatt cacctgcctt tcttgcaata aatgtttccg acagaagcaa cttctaaacg
1681 ctcacttcag gaaataccac gatgcaaatt tcatcccgac tgtttacaaa tgctccaagt
1741 gtggcaaagg cttttcccgc tggattaacc tgcacagaca ttcggagaag tgtggatcag
1801 gggaagcaaa gtcggctgct tcaggaaagg gaagaagaac aagaaagagg aagcagacca
```

-continued

```
1861 tcctgaagga agccacaaag ggtcagaagg aagctgcgaa gggatggaag gaagccgcga
1921 acggagacga agctgctgct gaggaggctt ccaccacgaa gggagaacag ttcccaggag
1981 agatgtttcc tgtcgcctgc agagaaacca cagccagagt caaagaggaa gtggatgaag
2041 gcgtgacctg tgaaatgctc ctcaacacga tggataagtg agagggattc gggttgcgtg
2101 ttcactgccc ccaattccta aagcaagtta gaagttttta gcatttaagg tgtgaaatgc
2161 tcctcaacac gatggataag tgagagagag tcaggttgca tgttcactgc ccctaattcc
2221 taaagcaagt tagaaatttt tagcattttc tttgaaacaa ttaagttcat gacaatggat
2281 gacacaagtt tgaggtagtg tctagaattg ttctcctgtt tgtagctgga tatttcaaag
2341 aaacattgca ggtattttat aaaagtttta aaccttgaat gagagggtaa cacctcaaac
2401 ctatggattc attcacttga tattggcaag gtggcccaca atgagtgagt agtgattttt
2461 ggatatttca aaatagtcta gaccagctag tgcttccaca gtcaaagctg gacattttta
2521 tgttgcatta tatacaccca tgatatttct aataatatat ggttttaaac attaaagaca
2581 aatgttttta tacaaatgaa ttttctacaa aatttaaagc taccataatg cttttaatta
2641 gttctaaatt caaccaaaaa atgtttact cttataaaaa ggaaaactga gtaggaaatg
2701 aaatactaga ttagactaga aaataaggaa taaatcgatt ttactttggt ataggagcaa
2761 ggttcacctt tagatttttg tattctcttt taattatgct ccttggcagg tatgaaattg
2821 ccctggttac attccattat tgcttattag tatttcactc cataacccct ttttctgcta
2881 aaactactct ttttatattt gtaaaataat tggcagagtg agaagaaaca taaaatcaga
2941 taaggcaaat gtgtacctgt aaggaatttg tacttttca taatgcccag tgattagtga
3001 gtatttccct tttgccagtt gacaagattt ttccacccctc gagcagcgtg agagatgcct
3061 ctttaacact tgaaattcat ttctatctgg atacagaggc agattttct tcattgctta
3121 gttgagcagt ttgttttgct gccaacctgt ctccacccct gtatttcaag atcattgata
3181 agccctaaat tcaaattctt aagatatgga ccttttattg aaaatatcac aagttcagaa
3241 tccctataca atgtgaatat gtggaaataa tttcccagca ggaagagcat tatattctct
3301 ttgtaccagc aaattaattt aactcaactc acatgagatt taaattctgt gggctgtagt
3361 atgccatcat tgtgactgaa tttgtgcaat ggtttcttaa ttttttact gttatttaaa
3421 gatgttttac ataattcaat aaaatgaaat gacttaaaat tgcaaaaaaa aaaaaaaaaa
3481 aaaaaaaaaa aaaaaaaaaa
```

Sequence description: amino acid sequence of Human BORIS (SEQ ID NO: 2)

MAATEISVLSEQFTKIKELELMPEKGLKEEEKDGVCREKDHRSPSELEAE

RTSGAFQDSVLEEEVELVLAPSEESEKYILTLQTVHFTSEAVELQDMSLL

SIQQQEGVQVVVQQPGPGLLWLEEGPRQSLQQCVAISIQQELYSPQEMEV

LQFHALEENVMVASEDSKLAVSLAETAGLIKLEEEQEKNQLLAERTKEQL

FFVETMSGDERSDEIVLTVSNSNVEEQEDQPTAGQADAEKAKSTKNQRKT

KGAKGTFHCDVCMFTSSRMSSFNRHMKTHTSEKPHLCHLCLKTFRTVTLL

RNHVNTHTGTRPYKCNDCNMAFVTSGELVRHRRYKHTHEKPFKCSMCKYA

SVEASKLKRHVRSHTGERPFQCCQCSYASRDTYKLKRHMRTHSGEKPYEC

HICHTRFTQSGTMKIHILQKHGENVPKYQCPHCATILARKSDLRVHMRNL

HAYSAAELKCRYCSAVFHERYALIQHQKTHKNEKRFKCKHCSYACKQERH

MTAHIRTHTGEKPFTCLSCNKCFRQKQLLNAHFRKYHDANFIPTVYKCSK

CGKGFSRWINLHRHSEKCGSGEAKSAASGKGRRTRKRKQTILKEATKGQK

EAAKGWKEAANGDEAAAEEASTTKGEQFPGEMFPVACRETTARVKEEVDE

GVTCEMLLNTMDK

Sequence description: amino acid sequence of Mouse BORIS
(SEQ ID NO: 4)

```
MAAAEVPVPSGYFTQIKEQKLKPGDLEEEKEEDGVQRVEAQEGVVKEVEAENSCLLLEAR      60
APVESDRRILTLQTVHLESQDVHLQGLGWLSVPHSEELSGTVPEAEGILQLPSVLWLDPE     120
PQLSLQHCVTVSIPEELYPPEELQRIHFHLLRENVLMAEENPELTPDLDESTALKKPEED     180
EKDQLPPQGETDKREERLLLLEMKPKEGKDDEIVLTISHLSLEEQQDPPAANQTSVPGAK     240
AAKPKRRRQTKGKPQSFQCDTCPFTSSKLSTFNRHIKIHSNERPHLCHLCLKAFRTVTLL     300
RNHVNTHTGTRPHKCRDCDMAFVTSGELVRHRRYKHTYEKPFKCSLCKYASVEASKMKRH     360
IRSHTGERPFQCCQCAYASRDSYKLKRHMRTHSGEKPYECPTCHVRFTQSGTMKIHIAQK     420
HGENVPKYECPHCATILARKSDLRVHLRNLHSQSPEEMKCRYCPAGFHERYALIQHQRTH     480
KNEKKFKCKQCDYACKQERCLKAHMRNHTGEKPFSCLACNKHFRQKQLLTVHLRKYHDPN     540
FVPNLHLCLKCDKRFSRWSNLQRHRKKCDPFHFTLAPNKDRRPVTRTQASEGEAGHKEGE     600
PQCPGEQALGHQGEAAGSQSPDHGLTCEMIFNMMDK
```

Sequence description: amino acid sequence of ZF deleted
Mouse BORIS (SEQ ID NO: 15)

```
MAAAEVPVPSGYFTQIKEQKLKPGDLEEEKEEDGVQRVEAQEGVVKEVEA
ENSCLLLEARAPVBSDRRILTLQTVHLESQDVHLQGLGWLSVPHSEELSG
TVPEAEGILQLPSVLWLDPEPQLSLQHCVTVSIPEELYPPEELQRIHFHL
LRENVLMAEENPELTPDLDESTALKKPEEDEKDQLPPQGETDKREERLLL
LEMKPKEGKDDEIVLTISHISLEEQQDPPAANQTSVPGAKAAKPKRRRQT
KGKPQSFQKLGGGGSGGGGSGGGGSGSETLAPNKDRRPVTRTQASEGEAG
HKEGEPQCPGEQALGHQGEAAGSQSPDHGLTCEMIFNMMDK
```

We claim:

1. An immunogenic composition comprising a polynucleotide encoding a nonfunctional mutant Brother of Regulator of Imprinted Sites (BORIS) protein, polypeptide or peptide, wherein said encoded protein, polypeptide or peptide comprises SEQ ID NO:2, lacking all zinc finger domains and is incapable of DNA binding.

2. The composition according to claim 1, wherein said nonfunctional mutant BORIS protein, polypeptide or peptide is attached to a pharmaceutically accepted carrier.

3. The composition according to claim 1, wherein said nonfunctional mutant BORIS protein, polypeptide or peptide is attached to a protein transducing domain.

4. The composition according to claim 1, further comprising an adjuvant.

5. The composition according to claim 4, wherein said adjuvant is mixed or fused to said polynucleotide encoding a nonfunctional mutant BORIS protein, polypeptide or peptide.

6. The composition according to claim 4, wherein said adjuvant is selected from the group consisting of a cytokine, a chemokine and a costimulatory molecule.

7. A vector comprising an immunogenic composition according to claim 1.

8. The vector of claim 7, wherein said vector allows expression in bacterial, mammalian, yeast or viral systems.

9. An immunotherapeutic composition against cancer comprising a polynucleotide encoding a nonfunctional mutant BORIS protein, polypeptide or peptide, wherein said encoded nonfunctional mutant BORIS protein, polypeptide or peptide comprises SEQ ID NO:2, lacking all zinc finger domains and is incapable of DNA binding.

10. The immunotherapeutic composition according to claim 9, further comprising an adjuvant.

11. The immunotherapeutic composition according to claim 9, further comprising an pharmaceutically acceptable carrier.

12. A method of producing an immune response in a mammalian subject which comprises administering to a patient in need thereof an effective amount of a polynucleotide encoding a ninfunctional mutant BORIS protien, polypeptide or peptide, wherein said encoded a nonfunctional mutant BORIS protien, polypeptide or peptide comprises SEQ ID NO:2, lacking all zinc finger domains and is incapable of DNA binding, to produce an immune response.

13. The method of claim 12, wherein said polynucleotide encoding a nonfunctional mutant BORIS protein, polypeptide or peptide is mixed or fused with a molecular adjuvant.

14. The method of claim 13, wherein said molecular adjuvant is a molecule that increases cellular immune response and/or antibody responses.

15. The method of claim 13, wherein said molecular adjuvant is selected from the group consisting of a cytokine, chemokine, costimulatory molecule.

16. The method of claim 12, wherein said polynucleotide encoding a nonfunctional mutant BORIS protein, polypeptide or peptide, is mixed with a conventional or molecular adjuvant.

17. The method of claim 12, wherein said nonfunctional mutant BORIS protein, polypeptide or peptide is attached to a pharmaceutically acceptable carrier.

18. The method of claim 12, wherein said nonfunctional mutant BORIS protein, polypeptide or peptide further comprises a protein transducing domain (PTD).

19. The method of claim 12, wherein said administration occurs intramuscularly, subcutaneously, intradermally, intravenously, nasally, rectally, vaginally or peritoneally.

20. The method according to claim 12, wherein said patient has more than one type of cancer.

21. The method of claim 12, wherein said patient has cancer.

22. The method of claim 21, wherein said cancer is breast or prostate cancer.

23. The method according to claim 12, wherein said immune response results from mounting a cellular immune response comprising T cells that recognize an epitope from a nonfunctional mutant BORIS peptide, polypeptide, or protien.

24. A method of treating cancer comprising administering to a patient in need thereof an effective amount of a polynucleotide encoding a nonfunctional mutant BORIS protein, polypeptide or peptide, wherein said encoded nonfunctional mutant BORIS protein, polypeptide or peptide comprises SEQ ID NO:2, lacking all zinc finger domains and is incapable of DNA binding.

* * * * *

```
                         SEQUENCE LISTING

<160> NUMBER OF SEQ ID NOS: 15

<210> SEQ ID NO 1
   <211> LENGTH: 3500
   <212> TYPE: DNA
   <213> ORGANISM: Homo sapien
   <220> FEATURE:
   <221> NAME/KEY: misc_feature
   <223> OTHER INFORMATION: wildtype nucleotide sequence of Human BORIS

<400> SEQUENCE: 1
ggcaccagac gcggtgcacg aggcagagcc acaagccaaa gacggagtgg gccgagcatt       60
ccggccacgc cttccgcggc caagtcatta tggcagccac tgagatctct gtcctttctg      120
agcaattcac caagatcaaa gaactcgagt tgatgccgga aaaaggcctg aaggaggagg      180
aaaaagacgg agtgtgcaga gagaaagacc atcggagccc tagtgagttg gaggccgagc      240
gtacctctgg ggccttccag gacagcgtcc tggaggaaga gtggagctg gtgctggccc       300 cctcggagga gagcgagaag tacatcctga ccctgcagac ggtgcacttc acttctgaag      360
ctgtggagtt gcaggatatg agcttgctga gcatacagca gcaagaaggg gtgcaggtgg      420
tggtgcaaca gcctggccct gggttgctgt ggcttgagga agggccccgg cagagcctgc      480
agcagtgtgt ggccattagt atccagcaag agctgtactc cccgcaagag atggaggtgt      540
tgcagttcca cgctctagag gagaatgtga tggtggccag tgaagacagt aagttagcgg      600
tgagcctggc tgaaactgct ggactgatca agctcgagga agagcaggag aagaaccagt      660
```

-continued

```
tattggctga aagaacaaag gagcagctct tttttgtgga aacaatgtca ggagatgaaa      720
gaagtgacga aattgttctc acagtttcaa attcaaatgt ggaagaacaa gaggatcaac      780
ctacagctgg tcaagcagat gctgaaaagg ccaaatctac aaaaaatcaa agaaagacaa      840
agggagcaaa aggaaccttc cactgtgatg tctgcatgtt cacctcttct agaatgtcaa      900
gttttaatcg tcatatgaaa actcacacca gtgagaagcc tcacctgtgt cacctctgcc      960
tgaaaacctt ccgtacggtc actctgctgc ggaaccatgt taacacccac acaggaacca     1020
ggccctacaa gtgtaacgac tgcaacatgg catttgtcac cagtggagaa ctcgtccgac     1080
acaggcgcta taaacatact catgagaaac cctttaaatg ttccatgtgc aagtatgcca     1140
gtgtggaggc aagtaaattg aagcgccatg tccgatccca cactggggag cgcccctttc     1200
agtgttgcca gtgcagctat gccagcgagA taccTacaa gctgaaacgc cacatgagaa     1260
cgcactcagg tgagaagcct tacgaatgcc acatctgcca cacccgcttc acccagagcg     1320
ggaccatgaa aatacatatt ctgcagaaac acggcgaaaa tgtccccaaa taccagtgtc     1380
cccattgtgc caccatcatt gcacggaaaa gcgacctacg tgtgcatatg cgcaacttgc     1440
atgcttacag cgctgcagag ctgaaatgcc gctactgttc tgctgtcttc catgaacgct     1500
atgccctcat tcagcaccag aaaactcata agaatgagaa gaggttcaag tgcaaacact     1560
gcagttatgc ctgcaagcag gaacgtcata tgaccgctca cattcgtacc cacactggag     1620
agaaaccatt cacctgcctt tcttgcaata aatgtttccg acagaagcaa cttctaaacg     1680
ctcacttcag gaaataccac gatgcaaatt tcatcccgac tgtttacaaa tgctccaagt     1740
gtggcaaagg cttttcccgc tggattaacc tgcacagaca ttcggagaag tgtggatcag     1800
gggaagcaaa gtcggctgct tcaggaaagg gaagaagaac aagaaagagg aagcagacca     1860
tcctgaagga agccacaaag ggtcagaagg aagctgcgaa gggatggaag gaagccgcga     1920
acggagacga agctgctgct gaggaggctt ccaccacgaa gggagaacag ttcccaggag     1980
agatgtttcc tgtcgcctgc agagaaacca cagccagagt caaagaggaa gtggatgaag     2040
gcgtgacctg tgaaatgctc ctcaacacga tggataagtg agagggattc gggttgcgtg     2100

ttcactgccc ccaattccta aagcaagtta gaagtttta gcatttaagg tgtgaaatgc     2160

tcctcaacac gatggataag tgagagagag tcaggttgca tgttcactgc cctaattcc     2220

taaagcaagt tagaaatttt tagcattttc tttgaaacaa ttaagttcat gacaatggat     2280
gacacaagtt tgaggtagtg tctagaattg ttctcctgtt tgtagctgga tattcaaag     2340 aaacattgca ggtattttat aaaagtttta aacttgaat gagagggtaa cacctcaaac     2400
ctatggattc attcacttga tattggcaag gtggcccaca atgagtgagt agtgattttt     2460
ggatatttca aaatagtcta gaccagctag tgcttccaca gtcaaagctg gacatttta     2520 tgttgcatta tatacaccca tgatatttct aatatat ggttttaaac attaagaca     2580 aatgttttta tacaaatgaa ttttctacaa aattaaagc taccataatg cttttaatta     2640
gttctaaatt caaccaaaaa atgttttact cttattaaaa ggaaaactga gtaggaaatg     2700
aaatactaga ttagactaga aaataaggaa taaatcgatt ttactttggt ataggagcaa     2760
ggttcacctt tagatttttg tattctcttt taattatgct ccttggcagg tatgaaattg     2820
ccctggttac attccatat tgcttattag tattcactc cataaccctt ttttctgcta     2880
aaactactct ttttatattt gtaaaataat tggcagagtg agaagaaaca taaaatcaga     2940

taaggcaaat gtgtacctgt aaggaatttg tactttttca taatgcccag tgattagtga     3000
gtatttccct tttgccagtt gacaagaтттт ttccaccctc gagcagcgtg agagatgcct     3060
```

```
ctttaacact tgaaattcat ttctatctgg atacagaggc agattttct tcattgctta      3120 gttgagcagt ttgttttgct gccaacctgt ctccaccct gtatttcaag atcattgata       3180
agccctaaat tcaaattctt aagatatgga ccttttattg aaaatatcac aagttcagaa      3240
tccctataca atgtgaatat gtggaaataa tttcccagca ggaagagcat tatattctct      3300
ttgtaccagc aaattaattt aactcaactc acatgagatt taaattctgt gggctgtagt      3360
atgccatcat tgtgactgaa tttgtgcaat ggtttcttaa ttttttttact gttatttaaa     3420 gatgttttac ataattcaat aaaatgaaat gacttaaaat tgcaaaaaaa aaaaaaaaa       3480 aaaaaaaaaa aaaaaaaaa                                                   3500

<210> SEQ ID NO 2
<211> LENGTH: 663
<212> TYPE: PRT
<213> ORGANISM: Homo sapien
<220> FEATURE:
<221> NAME/KEY: misc_feature
<223> OTHER INFORMATION: amino acid sequence of Human BORIS

<400> SEQUENCE: 2

Met Ala Ala Thr Glu Ile Ser Val Leu Ser Glu Gln Phe Thr Lys Ile
1               5                   10                  15

Lys Glu Leu Glu Leu Met Pro Glu Lys Gly Leu Lys Glu Glu Glu Lys
                20                  25                  30

Asp Gly Val Cys Arg Glu Lys Asp His Arg Ser Pro Ser Glu Leu Glu
            35                  40                  45

Ala Glu Arg Thr Ser Gly Ala Phe Gln Asp Ser Val Leu Glu Glu Glu
        50                  55                  60

Val Glu Leu Val Leu Ala Pro Ser Glu Glu Ser Glu Lys Tyr Ile Leu
65                  70                  75                  80

Thr Leu Gln Thr Val His Phe Thr Ser Glu Ala Val Glu Leu Gln Asp
                85                  90                  95

Met Ser Leu Leu Ser Ile Gln Gln Gln Glu Gly Val Gln Val Val Val
            100                 105                 110

Gln Gln Pro Gly Pro Gly Leu Leu Trp Leu Glu Glu Gly Pro Arg Gln
        115                 120                 125

Ser Leu Gln Gln Cys Val Ala Ile Ser Ile Gln Gln Glu Leu Tyr Ser
    130                 135                 140

Pro Gln Glu Met Glu Val Leu Gln Phe His Ala Leu Glu Glu Asn Val
145                 150                 155                 160

Met Val Ala Ser Glu Asp Ser Lys Leu Ala Val Ser Leu Ala Glu Thr
                165                 170                 175

Ala Gly Leu Ile Lys Leu Glu Glu Glu Gln Glu Lys Asn Gln Leu Leu
            180                 185                 190

Ala Glu Arg Thr Lys Glu Gln Leu Phe Phe Val Glu Thr Met Ser Gly
        195                 200                 205

Asp Glu Arg Ser Asp Glu Ile Val Leu Thr Val Ser Asn Ser Asn Val
    210                 215                 220

Glu Glu Gln Glu Asp Gln Pro Thr Ala Gly Gln Ala Asp Ala Glu Lys
225                 230                 235                 240

Ala Lys Ser Thr Lys Asn Gln Arg Lys Thr Lys Gly Ala Lys Gly Thr
                245                 250                 255

Phe His Cys Asp Val Cys Met Phe Thr Ser Ser Arg Met Ser Ser Phe
            260                 265                 270
```

-continued

```
Asn Arg His Met Lys Thr His Thr Ser Glu Lys Pro His Leu Cys His
            275                 280                 285

Leu Cys Leu Lys Thr Phe Arg Thr Val Thr Leu Leu Arg Asn His Val
    290                 295                 300

Asn Thr His Thr Gly Thr Arg Pro Tyr Lys Cys Asn Asp Cys Asn Met
305                 310                 315                 320

Ala Phe Val Thr Ser Gly Glu Leu Val Arg His Arg Arg Tyr Lys His
                325                 330                 335

Thr His Glu Lys Pro Phe Lys Cys Ser Met Cys Lys Tyr Ala Ser Val
            340                 345                 350

Glu Ala Ser Lys Leu Lys Arg His Val Arg Ser His Thr Gly Glu Arg
        355                 360                 365

Pro Phe Gln Cys Gln Cys Ser Tyr Ala Ser Arg Asp Thr Tyr Lys
    370                 375                 380

Leu Lys Arg His Met Arg Thr His Ser Gly Glu Lys Pro Tyr Glu Cys
385                 390                 395                 400

His Ile Cys His Thr Arg Phe Thr Gln Ser Gly Thr Met Lys Ile His
                405                 410                 415

Ile Leu Gln Lys His Gly Glu Asn Val Pro Lys Tyr Gln Cys Pro His
            420                 425                 430

Cys Ala Thr Ile Ile Ala Arg Lys Ser Asp Leu Arg Val His Met Arg
        435                 440                 445

Asn Leu His Ala Tyr Ser Ala Ala Glu Leu Lys Cys Arg Tyr Cys Ser
    450                 455                 460

Ala Val Phe His Glu Arg Tyr Ala Leu Ile Gln His Gln Lys Thr His
465                 470                 475                 480

Lys Asn Glu Lys Arg Phe Lys Cys Lys His Cys Ser Tyr Ala Cys Lys
                485                 490                 495

Gln Glu Arg His Met Thr Ala His Ile Arg Thr His Thr Gly Glu Lys
            500                 505                 510

Pro Phe Thr Cys Leu Ser Cys Asn Lys Cys Phe Arg Gln Lys Gln Leu
        515                 520                 525

Leu Asn Ala His Phe Arg Lys Tyr His Asp Ala Asn Phe Ile Pro Thr
    530                 535                 540

Val Tyr Lys Cys Ser Lys Cys Gly Lys Gly Phe Ser Arg Trp Ile Asn
545                 550                 555                 560

Leu His Arg His Ser Glu Lys Cys Gly Ser Gly Glu Ala Lys Ser Ala
                565                 570                 575

Ala Ser Gly Lys Gly Arg Arg Thr Arg Lys Arg Lys Gln Thr Ile Leu
            580                 585                 590

Lys Glu Ala Thr Lys Gly Gln Lys Glu Ala Ala Lys Gly Trp Lys Glu
        595                 600                 605

Ala Ala Asn Gly Asp Glu Ala Ala Glu Glu Ala Ser Thr Thr Lys
    610                 615                 620

Gly Glu Gln Phe Pro Gly Glu Met Phe Pro Val Ala Cys Arg Glu Thr
625                 630                 635                 640

Thr Ala Arg Val Lys Glu Glu Val Asp Glu Gly Val Thr Cys Glu Met
                645                 650                 655

Leu Leu Asn Thr Met Asp Lys
            660

<210> SEQ ID NO 3
<211> LENGTH: 2337
<212> TYPE: DNA
```

<213> ORGANISM: Mus musculus
<220> FEATURE:
<221> NAME/KEY: misc_feature
<223> OTHER INFORMATION: wildtype nucleotide sequence of mouse BORIS

<400> SEQUENCE: 3

| | | | | | |
|---|---|---|---|---|---|
| ccattttgtg | caccttgatc | aaagcccatg | tctactaggc | cccagcacct | ctgcacccca | 60 |
| taaagattgc | acgctctttt | tccatcaggg | gtcgtcacca | tggctgccgc | tgaggtccct | 120 |
| gtcccttctg | ggtacttcac | ccagatcaaa | gagcagaagt | tgaagcctgg | agacctagag | 180 |
| gaggagaaag | aggaggacgg | ggtacaaaga | gtggaagccc | aggagggagt | tgtcaaggag | 240 |
| gtggaggccg | agaacagttg | cctgcttctg | gaggccaggg | ccccggtgga | gagcgacagg | 300 |
| cggatcctga | ccctgcaaac | ggtgcacctg | gagtcccagg | atgtgcacct | acagggctg | 360 |
| ggatggctga | gcgtgccaca | ctctgaggag | ctttcaggga | cggtaccaga | ggcggaaggc | 420 |
| atactgcagt | tgccatccgt | gctgtggctc | gacccagagc | cccagctcag | ccttcagcat | 480 |
| tgcgtgacgg | tcagcatccc | ggaagagctg | tacccaccag | aggagctgca | gcggatacat | 540 |
| tttcacctgc | tgagagagaa | tgtgctaatg | gccgaggaga | acccagagtt | aacaccagac | 600 |
| ttggacgaaa | gcacagccct | gaaaaagccc | gaagaagatg | aaaaggacca | gctcccgccc | 660 |
| cagggagaga | cagacaagag | agaagagagg | ttgctccttc | tggaaatgaa | accaaaagag | 720 |
| ggaaaagacg | acgaaattgt | cctgaccatt | tcccatctaa | gcctcgaaga | cagcaagat | 780 |
| ccaccagcgg | ccaatcagac | aagtgtgccg | ggagccaaag | ccgcaaaacc | aaaacggcgg | 840 |
| aggcagacca | agggaaagcc | tcagagcttt | cagtgtgaca | cctgcccgtt | cacttcctcc | 900 |
| aagctctcaa | ctttcaatcg | tcacatcaaa | attcacagca | atgagaggcc | acacctgtgt | 960 |
| cacctgtgcc | tgaaggcctt | ccggactgtc | actcttctta | ggaaccatgt | gaacacccac | 1020 |
| acaggaacca | ggccccacaa | gtgcagggac | tgcgacatgg | cgtttgtcac | cagcggagaa | 1080 |
| ctcgtccggc | acaggcgtta | caaacacact | tatgagaagc | ccttcaagtg | ctccctgtgc | 1140 |
| aagtacgcca | gcgtcgaggc | aagcaagatg | aagcgtcaca | tccgctcaca | cacgggtgag | 1200 |
| cgtcccttcc | agtgttgcca | gtgtgcttat | gccagcaggg | actcctacaa | gctgaagcgc | 1260 |
| cacatgagga | cacactcagg | tgagaagccg | tatgaatgtc | ccacctgtca | cgtccggttc | 1320 |
| acccagagcg | ggaccatgaa | aatccatata | gcacagaagc | acggagagaa | tgtgcccaaa | 1380 |
| tacgagtgtc | cccactgtgc | caccatcatc | gcgaggaaga | gcgacctgcg | tgtccatctg | 1440 |
| cgtaacctgc | acagccagag | cccggaggag | atgaagtgcc | gatactgtcc | cgctggcttc | 1500 |
| catgagcgct | atgccctcat | tcagcaccag | aggacccaca | agaacgagaa | gaagttcaag | 1560 |
| tgcaagcagt | gcgattacgc | gtgcaagcag | gagcgatgct | tgaaggcgca | catgcgcatg | 1620 |
| cacacaggag | agaagcccctt | ctcctgcctg | gcctgcaaca | agcacttccg | acagaagcag | 1680 |
| ctactgaccg | tgcacctgag | gaagtaccat | gacccgaact | tcgtccccaa | tctgcacctg | 1740 |
| tgcctcaagt | gtgataaacg | tttctcccgc | tggagtaacc | tgcagagaca | cagaaagaag | 1800 |
| tgtgacccgg | agcatgagac | gttagcccccc | aacaaggaca | ggagaccagt | gacaaggaca | 1860 |
| caggcctcgg | agggagaagc | aggacacaag | gaaggggagc | ctcagtgccc | tggggagcag | 1920 |
| gctctgggcc | accaaggaga | agcagcgggg | agccagagcc | cagaccacgg | ccttacctgc | 1980 |
| gagatgatct | ttaacatgat | ggataagtga | tggataagtg | agcagtcgtg | cctctccgtg | 2040 |
| cagtggcctc | tggggaaga | aaccagttag | aaataagttc | ccagacacag | cacagtgttc | 2100 |
| tcagagtttg | agatagtgtg | tagaaatgtt | tgagagaagg | ggaaaaaaac | cctgcagcta | 2160 |

-continued

```
tttccaaaga cttgagtcag agctcgaagt gaaggtgcac atatctgggc cctagcaggt    2220
gcccagaatg agtcagggac agattctagg tgatacttat gtccacgggg gctcagacca    2280
gttaacgcct tggtggtcag agcagaaaat tttttgagtt gttgtaccca ccctcaa      2337
```

<210> SEQ ID NO 4
<211> LENGTH: 636
<212> TYPE: PRT
<213> ORGANISM: Mus musculus
<220> FEATURE:
<221> NAME/KEY: misc_feature
<223> OTHER INFORMATION: amino acid sequence of mouse BORIS

<400> SEQUENCE: 4

```
Met Ala Ala Ala Glu Val Pro Val Pro Ser Gly Tyr Phe Thr Gln Ile
1               5                   10                  15

Lys Glu Gln Lys Leu Lys Pro Gly Asp Leu Glu Glu Glu Lys Glu Glu
            20                  25                  30

Asp Gly Val Gln Arg Val Glu Ala Gln Glu Gly Val Val Lys Glu Val
        35                  40                  45

Glu Ala Glu Asn Ser Cys Leu Leu Glu Ala Arg Ala Pro Val Glu
    50                  55                  60

Ser Asp Arg Arg Ile Leu Thr Leu Gln Thr Val His Leu Glu Ser Gln
65                  70                  75                  80

Asp Val His Leu Gln Gly Leu Gly Trp Leu Ser Val Pro His Ser Glu
                85                  90                  95

Glu Leu Ser Gly Thr Val Pro Glu Ala Glu Gly Ile Leu Gln Leu Pro
            100                 105                 110

Ser Val Leu Trp Leu Asp Pro Glu Pro Gln Leu Ser Leu Gln His Cys
        115                 120                 125

Val Thr Val Ser Ile Pro Glu Glu Leu Tyr Pro Pro Glu Glu Leu Gln
    130                 135                 140

Arg Ile His Phe His Leu Leu Arg Glu Asn Val Leu Met Ala Glu Glu
145                 150                 155                 160

Asn Pro Glu Leu Thr Pro Asp Leu Asp Glu Ser Thr Ala Leu Lys Lys
                165                 170                 175

Pro Glu Glu Asp Glu Lys Asp Gln Leu Pro Pro Gln Gly Glu Thr Asp
            180                 185                 190

Lys Arg Glu Glu Arg Leu Leu Leu Leu Glu Met Lys Pro Lys Glu Gly
        195                 200                 205

Lys Asp Asp Glu Ile Val Leu Thr Ile Ser His Leu Ser Leu Glu Glu
    210                 215                 220

Gln Gln Asp Pro Pro Ala Ala Asn Gln Thr Ser Val Pro Gly Ala Lys
225                 230                 235                 240

Ala Ala Lys Pro Lys Arg Arg Gln Thr Lys Gly Lys Pro Gln Ser
                245                 250                 255

Phe Gln Cys Asp Thr Cys Pro Phe Thr Ser Ser Lys Leu Ser Thr Phe
            260                 265                 270

Asn Arg His Ile Lys Ile His Ser Asn Glu Arg Pro His Leu Cys His
        275                 280                 285

Leu Cys Leu Lys Ala Phe Arg Thr Val Thr Leu Leu Arg Asn His Val
    290                 295                 300

Asn Thr His Thr Gly Thr Arg Pro His Lys Cys Arg Asp Cys Asp Met
305                 310                 315                 320

Ala Phe Val Thr Ser Gly Glu Leu Val Arg His Arg Arg Tyr Lys His
                325                 330                 335
```

```
Thr Tyr Glu Lys Pro Phe Lys Cys Ser Leu Cys Lys Tyr Ala Ser Val
            340                 345                 350

Glu Ala Ser Lys Met Lys Arg His Ile Arg Ser His Thr Gly Glu Arg
            355                 360                 365

Pro Phe Gln Cys Cys Gln Cys Ala Tyr Ala Ser Arg Asp Ser Tyr Lys
            370                 375                 380

Leu Lys Arg His Met Arg Thr His Ser Gly Glu Lys Pro Tyr Glu Cys
385                 390                 395                 400

Pro Thr Cys His Val Arg Phe Thr Gln Ser Gly Thr Met Lys Ile His
                405                 410                 415

Ile Ala Gln Lys His Gly Glu Asn Val Pro Lys Tyr Glu Cys Pro His
            420                 425                 430

Cys Ala Thr Ile Ile Ala Arg Lys Ser Asp Leu Arg Val His Leu Arg
            435                 440                 445

Asn Leu His Ser Gln Ser Pro Glu Glu Met Lys Cys Arg Tyr Cys Pro
            450                 455                 460

Ala Gly Phe His Glu Arg Tyr Ala Leu Ile Gln His Gln Arg Thr His
465                 470                 475                 480

Lys Asn Glu Lys Lys Phe Lys Cys Lys Gln Cys Asp Tyr Ala Cys Lys
                485                 490                 495

Gln Glu Arg Cys Leu Lys Ala His Met Arg Asn His Thr Gly Glu Lys
            500                 505                 510

Pro Phe Ser Cys Leu Ala Cys Asn Lys His Phe Arg Gln Lys Gln Leu
            515                 520                 525

Leu Thr Val His Leu Arg Lys Tyr His Asp Pro Asn Phe Val Pro Asn
            530                 535                 540

Leu His Leu Cys Leu Lys Cys Asp Lys Arg Phe Ser Arg Trp Ser Asn
545                 550                 555                 560

Leu Gln Arg His Arg Lys Lys Cys Asp Pro Phe His Phe Thr Leu Ala
                565                 570                 575

Pro Asn Lys Asp Arg Arg Pro Val Thr Arg Thr Gln Ala Ser Glu Gly
            580                 585                 590

Glu Ala Gly His Lys Glu Gly Glu Pro Gln Cys Pro Gly Glu Gln Ala
            595                 600                 605

Leu Gly His Gln Gly Glu Ala Ala Gly Ser Gln Ser Pro Asp His Gly
            610                 615                 620

Leu Thr Cys Glu Met Ile Phe Asn Met Met Asp Lys
625                 630                 635

<210> SEQ ID NO 5
<211> LENGTH: 29
<212> TYPE: DNA
<213> ORGANISM: Artificial Sequence
<220> FEATURE:
<223> OTHER INFORMATION: MB1F primer used in RT-PCR

<400> SEQUENCE: 5
cgtcaccatg gctgccgctg aggtccctg                                       29

<210> SEQ ID NO 6
<211> LENGTH: 32
<212> TYPE: DNA
<213> ORGANISM: Artificial Sequence
<220> FEATURE:
<223> OTHER INFORMATION: MB1R primer used in RT-PCR

<400> SEQUENCE: 6
```

```
aagcttctga aagctctgag gctttccctt gg                              32

<210> SEQ ID NO 7
<211> LENGTH: 33
<212> TYPE: DNA
<213> ORGANISM: Artificial Sequence
<220> FEATURE:
<223> OTHER INFORMATION: MB2F primer used in RT-PCR

<400> SEQUENCE: 7
ggatccgaga cgttagcccc caacaaggac agg                             33

<210> SEQ ID NO 8
<211> LENGTH: 41
<212> TYPE: DNA
<213> ORGANISM: Artificial Sequence
<220> FEATURE:
<223> OTHER INFORMATION: MB2R primer used in RT-PCR

<400> SEQUENCE: 8
gaattctcac ttatccatca tgttaaagat catctcgcag g                    41

<210> SEQ ID NO 9
<211> LENGTH: 51
<212> TYPE: DNA
<213> ORGANISM: Artificial Sequence
<220> FEATURE:
<223> OTHER INFORMATION: SpF primer used in RT-PCR

<400> SEQUENCE: 9
agcttggtgg aggcggttca ggcggaggtg gctctggcgg tggcggatcg g         51

<210> SEQ ID NO 10
<211> LENGTH: 51
<212> TYPE: DNA
<213> ORGANISM: Artificial Sequence
<220> FEATURE:
<223> OTHER INFORMATION: SpR primer used in RT-PCR

<400> SEQUENCE: 10
gatcccgatc cgccaccgcc agagccacct ccgcctgaac cgcctccacc a         51

<210> SEQ ID NO 11
<211> LENGTH: 43
<212> TYPE: DNA
<213> ORGANISM: Artificial Sequence
<220> FEATURE:
<223> OTHER INFORMATION: SalI-MB-F primer used to synthesize the BORIS
      fragment by PCR

<400> SEQUENCE: 11
acgcgtcgac atggctgccg ctgaggtccc tgtcccttct ggg                  43

<210> SEQ ID NO 12
<211> LENGTH: 41
<212> TYPE: DNA
<213> ORGANISM: Artificial Sequence
<220> FEATURE:
<223> OTHER INFORMATION: NotI-MB-R primer used to synthesize the BORIS
      fragment by PCR

<400> SEQUENCE: 12
cggccgtcac ttatccatca tgttaaagat catctcgcag g                    41

<210> SEQ ID NO 13
```

```
<211> LENGTH: 11
<212> TYPE: PRT
<213> ORGANISM: Artificial Sequence
<220> FEATURE:
<223> OTHER INFORMATION: HIV-Tat protein transduction domain

<400> SEQUENCE: 13

Tyr Gly Arg Lys Lys Arg Arg Gln Arg Arg Arg
1               5                   10

<210> SEQ ID NO 14
<211> LENGTH: 1026
<212> TYPE: DNA
<213> ORGANISM: Artificial Sequence
<220> FEATURE:
<223> OTHER INFORMATION: nucleotide sequence of ZF deleted BORIS
      molecule

<400> SEQUENCE: 14
atggctgccg ctgaggtccc tgtcccttct gggtacttca cccagatcaa agagcagaag      60
ttgaagcctg gagacctaga ggaggagaaa gaggaggacg gggtacaaag agtggaagcc     120 caggaggag ttgtcaagga ggtggaggcc gagaacagtt gcctgcttct ggaggccagg      180
gccccggtgg agagcgacag gcggatcctg accctgcaaa cggtgcacct ggagtcccag     240
gatgtgcacc tacagggggct gggatggctg agcgtgccac actctgagga gctttcaggg    300
acggtaccag aggcggaagg catactgcag ttgccatccg tgctgtggct cgacccagag     360
ccccagctca gccttcagca ttgcgtgacg gtcagcatcc ggaagagct gtacccacca     420 gaggagctgc agcggataca ttttcacctg ctgagagaga atgtgctaat ggccgaggag     480
aacccagagt taacaccaga cttggacgaa agcacagccc tgaaaaagcc cgaagaagat     540
gaaaaggacc agctcccgcc ccagggagag acagacaaga gagaagagag gttgctcctt     600
ctggaaatga aaccaaaaga gggaaaagac gacgaaattg tcctgaccat ttcccatcta     660
agcctcgaag aacagcaaga tccaccagcg gccaatcaga caagtgtgcc gggagccaaa     720
gccgcaaaac caaaacggcg gaggcagacc aagggaaagc ctcagagctt tcagaagctt     780
ggtggaggcg gttcaggcgg aggtggctct ggcggtggcg gatcgggatc cgagacgtta     840
gcccccaaca aggacaggag accagtgaca aggacacagg cctcggaggg agaagcagga     900
cacaaggaag gggagcctca gtgccctggg gagcaggctc tgggccacca aggagaagca     960
gcggggagcc agagcccaga ccacggcctt acctgcgaga tgatctttaa catgatggat    1020
aagtga                                                              1026

<210> SEQ ID NO 15
<211> LENGTH: 341
<212> TYPE: PRT
<213> ORGANISM: Mus musculus
<214> FEATURE:
<221> NAME/KEY: misc_feature
<223> OTHER INFORMATION: amino acid sequence of ZF deleted mouse BORIS

<400> SEQUENCE: 15

Met Ala Ala Ala Glu Val Pro Val Pro Ser Gly Tyr Phe Thr Gln Ile
1               5                   10                  15

Lys Glu Gln Lys Leu Lys Pro Gly Asp Leu Glu Glu Glu Lys Glu Glu
                20                  25                  30

Asp Gly Val Gln Arg Val Glu Ala Gln Glu Gly Val Val Lys Glu Val
            35                  40                  45

Glu Ala Glu Asn Ser Cys Leu Leu Leu Glu Ala Arg Ala Pro Val Glu
```

-continued

```
            50                  55                  60
Ser Asp Arg Arg Ile Leu Thr Leu Gln Thr Val His Leu Glu Ser Gln
65                  70                  75                  80

Asp Val His Leu Gln Gly Leu Gly Trp Leu Ser Val Pro His Ser Glu
                85                  90                  95

Glu Leu Ser Gly Thr Val Pro Glu Ala Glu Gly Ile Leu Gln Leu Pro
                100                 105                 110

Ser Val Leu Trp Leu Asp Pro Glu Pro Gln Leu Ser Leu Gln His Cys
                115                 120                 125

Val Thr Val Ser Ile Pro Glu Glu Leu Tyr Pro Pro Glu Glu Leu Gln
                130                 135                 140

Arg Ile His Phe His Leu Leu Arg Glu Asn Val Leu Met Ala Glu Glu
145                 150                 155                 160

Asn Pro Glu Leu Thr Pro Asp Leu Asp Glu Ser Thr Ala Leu Lys Lys
                165                 170                 175

Pro Glu Glu Asp Glu Lys Asp Gln Leu Pro Pro Gln Gly Glu Thr Asp
                180                 185                 190

Lys Arg Glu Glu Arg Leu Leu Leu Leu Glu Met Lys Pro Lys Glu Gly
                195                 200                 205

Lys Asp Asp Glu Ile Val Leu Thr Ile Ser His Leu Ser Leu Glu Glu
                210                 215                 220

Gln Gln Asp Pro Pro Ala Ala Asn Gln Thr Ser Val Pro Gly Ala Lys
225                 230                 235                 240

Ala Ala Lys Pro Lys Arg Arg Gln Thr Lys Gly Lys Pro Gln Ser
                245                 250                 255

Phe Gln Lys Leu Gly Gly Gly Ser Gly Gly Gly Gly Ser Gly Gly
                260                 265                 270

Gly Gly Ser Gly Ser Glu Thr Leu Ala Pro Asn Lys Asp Arg Arg Pro
                275                 280                 285

Val Thr Arg Thr Gln Ala Ser Glu Gly Glu Ala Gly His Lys Glu Gly
                290                 295                 300

Glu Pro Gln Cys Pro Gly Glu Gln Ala Leu Gly His Gln Gly Glu Ala
305                 310                 315                 320

Ala Gly Ser Gln Ser Pro Asp His Gly Leu Thr Cys Glu Met Ile Phe
                325                 330                 335

Asn Met Met Asp Lys
                340
```